(12) United States Patent
Gauczinski et al.

(10) Patent No.: US 10,874,599 B2
(45) Date of Patent: Dec. 29, 2020

(54) COMPOSITION FOR INHIBITING MICRO-ORGANISMS

(71) Applicant: Clariant International Ltd., Muttenz (CH)

(72) Inventors: Jan Gauczinski, Freiburg (DE); Franz-Xaver Scherl, Burgkirchen (DE); Martin Knoebl, Burgkirchen (DE); Beate Siefer, Frankfurt am Main (DE); Ute Back, Blankenbach (DE); Joerg Grohmann, Niedernhausen (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 16/869,986

(22) Filed: May 8, 2020

(65) Prior Publication Data

US 2020/0261342 A1    Aug. 20, 2020

Related U.S. Application Data

(63) Continuation of application No. 16/311,672, filed as application No. PCT/EP2017/065927 on Jun. 27, 2017.

(30) Foreign Application Priority Data

Jun. 29, 2016    (EP) ..................... 16176830

(51) Int. Cl.

| A61K 8/49 | (2006.01) |
| A01N 43/08 | (2006.01) |
| A61Q 19/00 | (2006.01) |
| A61K 8/34 | (2006.01) |
| A61Q 17/00 | (2006.01) |
| A61Q 19/10 | (2006.01) |
| A61Q 5/02 | (2006.01) |

(52) U.S. Cl.
CPC ............ A61K 8/4973 (2013.01); A01N 43/08 (2013.01); A61K 8/345 (2013.01); A61Q 17/005 (2013.01); A61Q 19/00 (2013.01); A61K 2800/10 (2013.01); A61K 2800/524 (2013.01); A61Q 5/02 (2013.01); A61Q 19/10 (2013.01)

(58) Field of Classification Search
CPC .................................................. A61K 8/4973
See application file for complete search history.

(56) References Cited

U.S. PATENT DOCUMENTS

| 1,985,424 A | 12/1934 | Piggott |
| 2,182,306 A | 12/1939 | Ulrich |
| 2,208,095 A | 7/1940 | Esselmann |
| 2,553,696 A | 5/1951 | Wilson |
| 2,806,839 A | 9/1957 | Crowther |
| 2,809,971 A | 10/1957 | Bernstein |
| 2,993,887 A | 7/1961 | Zech |
| 3,033,746 A | 5/1962 | Moyle |
| 3,236,733 A | 2/1966 | Karsten |
| 3,753,196 A | 8/1973 | Kurtz |
| 3,761,418 A | 9/1973 | Parran |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,470,982 A | 9/1984 | Winkler |
| 5,104,646 A | 4/1992 | Bolich, Jr. |
| 6,645,476 B1 | 11/2003 | Morschhaeuser |
| 2001/0029287 A1 | 10/2001 | Loffler |
| 2005/0002977 A1 | 1/2005 | Mallo |
| 2012/0100084 A1 | 4/2012 | Peter |
| 2012/0100085 A1* | 4/2012 | Klug ............... A01N 43/16 424/59 |

FOREIGN PATENT DOCUMENTS

| AU | 750044 | 3/2001 |
| CA | 2209060 | 12/1997 |
| CA | 2719451 | 10/2009 |
| DE | 102009014877 | 9/2009 |
| EP | 0550637 | 7/1993 |
| EP | 0816403 | 1/1998 |
| EP | 1069142 | 1/2001 |
| EP | 1084696 | 3/2001 |
| EP | 1116733 | 7/2001 |
| EP | 1347736 | 10/2003 |

(Continued)

OTHER PUBLICATIONS

International Search Report for PCT/EP2017/065927, dated Aug. 29, 2017, 2 pages.

*Primary Examiner* — Brian J Davis

(74) *Attorney, Agent, or Firm* — Tod A. Waldrop

(57) ABSTRACT

The present invention relates to a composition for inhibiting micro-organisms, as well as related processes, formulations, concentrates and uses. The composition comprises at least 30 wt.-% compound X, wherein compound X is according to Formula (I):

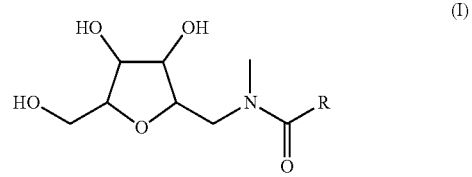

(I)

wherein R is a saturated or unsaturated hydrocarbon chain having seven or nine carbon atoms, or a mixture thereof.

19 Claims, No Drawings

(56) References Cited

FOREIGN PATENT DOCUMENTS

| | | |
|---|---|---|
| EP | 1496081 | 1/2005 |
| EP | 2105127 | 9/2009 |
| JP | H0753988 | 2/1995 |
| WO | 9206070 | 4/1992 |
| WO | 2007138054 | 12/2007 |
| WO | 2010136120 | 12/2010 |
| WO | 2013017262 | 2/2013 |
| WO | 2013178697 | 12/2013 |
| WO | 2013178700 | 12/2013 |
| WO | 2016146303 | 9/2016 |

* cited by examiner

COMPOSITION FOR INHIBITING MICRO-ORGANISMS

FIELD OF THE INVENTION

The present invention relates to a composition for inhibiting micro-organisms, as well as related processes, formulations, concentrates and uses.

BACKGROUND OF THE INVENTION

Preservation of household formulations, such as cosmetic formulations, extends their shelf life and therefore provides greater value for money for consumers. Furthermore, preservatives prevent consumers from distributing microbes around their home or on themselves and hence provide health benefits. Anti-microbial actives are well-described in the art and there are many available that provide excellent performance.

Klug et al. in US-2012/0100085A1 (2012, Clariant) discloses liquid compositions which contain a) from 5 to 95% by weight of sorbitan monocaprylate and b) from 5 to 95% by weight of one or more alcohols of the formula (1) disclosed therein. Klug et al. discusses in § 4 the objective of keeping the total amount of antimicrobially active alcohols in the cosmetic, dermatological or pharmaceutical formulation low and finding a dermatologically and toxicologically harmless substance that supports the antimicrobial action of the antimicrobially active alcohols in a synergistic manner. Klug et al. then goes on to state that it has been found that the sorbitan monocaprylate already known and used in cosmetics as a surfactant and emulsifying agent fulfills exactly these conditions.

However, there is a desire for providing an array of sophisticated preservation systems whereby excellent anti-microbial performance is provided and yet keeping the levels of preservation actives to a minimum. In line with the statements of Klug et al., many well-known preservation actives having excellent efficacy are not preferred e.g. due to reduced consumer acceptance, health worries or due to regulatory restrictions. The levels of such actives may also be (legally) restricted for the same reasons. Furthermore, there is a desire for all elements of preservation systems to meet sustainability goals and ensure that household formulations are as environmentally friendly as possible.

There is thus a need to provide even more sophisticated preservation systems, and elements thereof, that provide excellent anti-microbial effects and yet are highly accepted by consumers, do not raise health or regulatory concerns, and have excellent sustainability and environmentally friendly profiles.

SUMMARY OF THE INVENTION

In a first aspect, the present invention relates to a composition for inhibiting micro-organisms wherein the composition comprises at least 30 wt.-% compound X, wherein compound X is according to Formula (I):

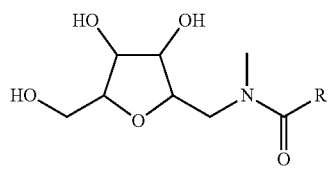

(I)

wherein R is a saturated or unsaturated hydrocarbon chain having seven or nine carbon atoms, or a mixture thereof.

DETAILED DESCRIPTION OF THE INVENTION

Definitions and General

In this document, including in all embodiments of all aspects of the present invention, the following definitions apply unless specifically stated otherwise. All percentages are by weight (w/w) of the total composition. All ratios are weight ratios. "wt.-%" means percentage by weight. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

"Molecular weight" or "M.Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than 1%, or less than 0.8%, or less than 0.5%, or less than 0.3%, or about 0%, by total weight of the composition or formulation.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

"Hairstyling polymer" means a hair-fixing polymer which forms a film on a surface i.e. a film-forming polymer. 'Hairstyling polymer' and 'film-forming polymer' are used interchangeably in the art. In the context of hair science, this surface is the surface of individual hair fibres or a plurality thereof. The hairstyling polymer causes the hair fibres to be glued together to build welds, which are effectively cross-links that provide the hold benefit. In concert, these welds form a 'hairnet' to provide hair hold and volume benefits to the consumer. When the net of welds is effectively formed, the hold and volume benefits can last all day and offer good resistance to environmental humidity.

Explanation of and Benefits Provided by the Invention

The present invention relates to a composition for inhibiting micro-organisms wherein the composition comprises compound X. Compound X relates to a specific type of fatty N-methyl cyclic glucamide(s). Surprisingly, it has now been found that such specific fatty N-methyl cyclic glucamides, are capable of inhibiting the growth of microorganisms.

Zech in U.S. Pat. No. 2,993,887 (1961, Atlas Powder Company) discloses "heterocyclic amides" and mentions that they can be "useful as chemical intermediates, emulsifiers, wetting and dispersing agents, dyeing assistants, antistatic agents, corrosion inhibitors, detergents, textile softeners and lubricants, lubricant additives". A generic Formula (I)s disclosed in column 1 of Zech having substituents R, R1 and R2, which may each be selected from a very long list of possible options. Claim 1 of Zech requires that R corresponds to the empirical formula $(C_6H_8(OH)_3O)$. There is no clear and unambiguously derivable disclosure in Zech of the present invention, neither from a chemical structure perspective nor purpose and effect perspective. Furthermore, the structures disclosed in the dependent claims of Zech as well as the description of the materials used in the examples of Zech, teach the skilled artisan away from the present invention.

Piggott in U.S. Pat. No. 1,985,424 (1934, ICI) discloses "textile assistants" and "ALKYLENE-OXIDE DERIVATIVES OF POLYHYDROXYALKYL-ALKYLAMIDES". There is no clear and unambiguously derivable disclosure in Piggott of the present invention, neither from a chemical structure perspective nor purpose and effect perspective. In particular, there is no explicit disclosure in Piggott of the specific type of fatty N-methyl cyclic glucamide herein claimed.

Yutaka et al. in JPH0753988 (1995, Lion) discloses a detergent composition. There is no clear and unambiguously derivable disclosure in Yutaka of the present invention, neither from a chemical structure perspective nor purpose and effect perspective.

Connor et al. in WO-92/06070 (1992, P&G) discloses a HIGH CATALYST PROCESS FOR GLUCAMIDE DETERGENTS. There is no clear and unambiguously derivable disclosure in Connor of the present invention, neither from a chemical structure perspective nor purpose and effect perspective. Furthermore, the skilled artisan is taught from the final clauses of claims 2 and 3 of Connor to avoid cyclic glucamide compounds.

The specific fatty N-methyl cyclic glucamides claimed herein are short alkyl chain polyols and represent amphiphilic compounds. The hydrophobic alkyl chain and the hydrophilic head group drive compound X into the interphases of oil/water, water/air, or water/phospholipid layers. The surface tension is thereby reduced. This allows interaction with cell walls, e.g. of microorganisms, and plays an important synergistic role in the mechanism of action of traditional preservatives. Compound X can stabilise oil/water interphases, e.g. by emulsifiying or solubilizing hydrophobic ingredients in polar solvents or modifying the viscosity of surfactant-based systems/surfactant solutions.

Regulatory restrictions in the field of preservatives have led to a smaller toolbox for formulators to preserve their formulations effectively. Synthetic and petroleum-based ingredients are under public scrutiny for many reasons, e.g. sustainability, safety, impurities, non-environmentally-friendly processes, waste generation, slow biodegradability, bad reputation amongst consumers. Lower amounts of preservatives have to be supported/improved in their preservation efficacy in order to provide sufficient protection against contamination of the formulation with microorganisms. Preservative boosters are used to overcome the gap in efficacy due to a reduction in the level of classical preservative used and boost the efficacy of preservatives synergistically. Commonly used preservative boosters are poorly water-soluble or completely water-insoluble. This makes formulating them difficult, as most formulations contain a high amount of water. Solubilisers may have to be used, to keep the ingredient in the formulation. Via the present invention, the cost of solubilisers can be saved, reducing formulation complexity and reducing storage need for more ingredients.

Indeed, the present invention provides excellent performance and provide the formulator with an excellent choice when deciding on a means for preserving the formulation. The specific type of fatty N-methyl cyclic glucamides of the present invention inhibit the growth of microorganisms thus extending options for formulators. Indeed, compound X is: water-soluble and can be dissolved at 1% in water to obtain a clear solution. Similarly, 10% of water can be dissolved in 90% of a composition of compound X to obtain a clear solution; it is stable at a pH range of pH 4-10 due to the amide bond, which offers superior stability versus commonly used esters; it can be synthesised in a cost effective reaction without the need for process aids (during amidation). Another advantage lies in the fact that the compound X is a viscous liquid and can therefore easily be employed in a wide-variety of different formulations. Furthermore, the specific type of fatty N-methyl cyclic glucamides of the present invention are based in the renewable raw materials glucose and fatty acids, which offer a more sustainable solution that is also more sustainable than commonly used boosters such as ethylhexylglycerin (EHG) or octanediol. Moreover, glucose is more easily available than many other sugars and sugar-derived ingredients are highly understood and accepted by consumers. Furthermore, the specific type of fatty N-methyl cyclic glucamides of the present invention offer many other benefits. Due to their surfactant-like structure, they can act as a hydrotrope and also as a wetting agent. Also they can act as emulsifiers due to their high HLB non-ionic surfactant-like structure and as solubilisers for the same reason.

The details of the invention and its aspects are provided hereinafter.

First Aspect

The first aspect relates to a composition for inhibiting micro-organisms wherein the composition comprises at least 30 wt.-% compound X, wherein compound X is according to Formula (I):

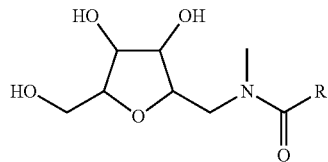

wherein R is a saturated or unsaturated hydrocarbon chain having seven or nine carbon atoms, or a mixture thereof. In at least one embodiment, the composition comprises a total amount of compound X being at least 30 wt.-% by total weight of the composition.

Compound X specific is a type of fatty N-methyl cyclic glucamide. Formula (I) encompasses multiple species of such specific fatty N-methyl cyclic glucamides in that R is a hydrocarbon chain that can be saturated or unsaturated and must have either seven or nine carbon atoms. In at least one embodiment, composition comprises at least 30 wt.-% compound X, wherein compound X is a combination of C7 and C9 compounds according to Formula (I). In at least one embodiment, compound X is a mixture of different compounds according to Formula (I) wherein R is —(CH$_2$)$_8$CH$_3$ or —(CH$_2$)$_6$CH$_3$.

In at least one embodiment, the composition comprises at least 40%, preferably at least 50%, more preferably at least 60%, even more preferably 70 wt.-%, even more preferably at least 80 wt.-%, most preferably at least 90 wt.-% compound X.

In at least one embodiment, the composition comprises a sole compound X according to Formula (I) and wherein R is a saturated or unsaturated hydrocarbon chain having seven or nine carbon atoms. In other words, the composition may comprise only one type of compound X according to Formula (I), wherein R is a saturated or unsaturated hydrocarbon chain having seven or nine carbon atoms. Having such a pure composition has the benefit that the chemical interactions with other ingredients can be more easily predicted. Furthermore, it is more desirable for consumers when an ingredient relates to one type of molecule rather than a more complex mixture.

It may be desirable for the composition to comprise a minimum amount of one particular species of compound X according to Formula (I), wherein R is a saturated or unsaturated hydrocarbon chain having seven or nine carbon atoms. In at least one embodiment, the composition comprises at least 15 wt.-% compound X, wherein compound X is according to Formula (I):

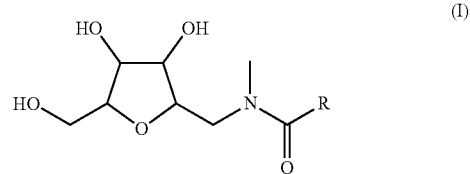

wherein R is —(CH$_2$)$_8$CH$_3$ or —(CH$_2$)$_6$CH$_3$. In at least one embodiment, the composition comprises at least 30 wt.-%, preferably at least 40 wt.-%, preferably at least 50 wt.-%, more preferably at least 60 wt.-%, even more preferably 70 wt.-%, even more preferably at least 80 wt.-%, most preferably at least 90 wt.-% compound X according to Formula (I), wherein R is —(CH$_2$)$_8$CH$_3$ or —(CH$_2$)$_6$CH$_3$.

In at least one embodiment, compound X is a mixture of different compounds according to Formula (I) wherein R is a saturated or unsaturated hydrocarbon chain having seven or nine carbon atoms, preferably wherein the weight ratio of C7:C9 is from 3:7 to 7:3, preferably from 4:6 to 6:4. It is desirable for a mixture of different compounds to be employed since purification steps can be avoided and/or more varied starting materials can be used. Indeed, increased purity normally correlates with increased expense. Hence a mixture of compounds may provide economic benefits.

In at least one embodiment, the composition is an aqueous solution.

In at least one embodiment, the composition comprises solvent. In at least one embodiment, the composition comprises a solvent, wherein the solvent comprises water and/or alcohol. Solvent is useful for providing the compounds used in present invention in liquid form. In at least one embodiment, the solvent is cosmetically acceptable. In at least one embodiment, the composition comprises at least 10 wt.-%, preferably at least 20 wt.-%, more preferably at least 30 wt.-%, even more preferably at least 50 wt.-% water. Water is useful for economic reasons but also because it is cosmetically acceptable. Optionally the composition comprises water-miscible or water-soluble solvents such as lower alkyl alcohols. In at least one embodiment, the composition comprises C$_1$-C$_5$ alkyl monohydric alcohols, preferably C$_2$-C$_3$ alkyl alcohols. The alcohols which may be present are in particular lower monohydric or polyhydric alcohols having 1 to 4 carbon atoms customarily used for cosmetic purposes, such as preferably ethanol and isopropanol.

Optionally, the composition comprises a water-soluble polyhydric alcohol. In at least one embodiment, the water-soluble polyhydric alcohols are polyhydric alcohols having two or more hydroxyl groups in the molecule. In at least one embodiment, the water-soluble polyhydric alcohol is selected from the group consisting of: dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether, and mixtures thereof.

In a preferred embodiment, the composition comprises a solvent selected from the group consisting of water, glycols, ethanol, and combinations thereof.

In a preferred embodiment, the composition comprises an aqueous, alcoholic or aqueous-alcoholic solvent, and wherein the aqueous, alcoholic or aqueous-alcoholic solvent comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof; more preferably wherein the aqueous, alcoholic or aqueous-alcoholic solvent comprises water, isopropanol, 1,2-propylene glycol, 1,3-propylene glycol, or mixtures thereof; even more preferably wherein the aqueous, alcoholic or aqueous-alcoholic solvent consists of water or consists of a mixture of water and an alcohol wherein the alcohol is selected from the group consisting of isopropanol, 1,2-propylene glycol and 1,3-propylene glycol.

Natural solvents can also be used. In at least one embodiment, the composition comprises a solvent selected from the group consisting of plant oil, honey, plant-derived sugar compositions, and mixtures thereof.

In at least one embodiment, the composition is a pumpable liquid. In at least one embodiment, the composition is paste-like.

In at least one embodiment, the viscosity of the composition is from 1 mPa·s to 20,000 mPa·s.

In at least one embodiment, the composition is the composition, besides compound X, is substantially free of any anti-microbial active. Anti-microbial actives are discussed in more detail in the third aspect.

Example Embodiments of the First Aspect:

In a preferred embodiment, the first aspect relates to a composition for inhibiting micro-organisms wherein the composition comprises at least 60 wt.-% compound X, wherein compound X is according to Formula (I):

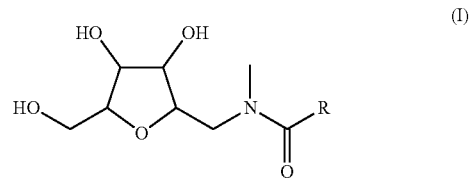

wherein R is —$(CH_2)_8CH_3$ or —$(CH_2)_6CH_3$, or a mixture thereof;

and wherein the composition is an aqueous solution.

Second Aspect

A second aspect relates to a process for synthesising the composition according to the first aspect comprising:
(a) Contacting N-methyl-glucamine with octanoic acid, decanoic acid or a mixture thereof, to form a reaction blend;
(b) Heating the reaction blend to boil off any water;
(c) Allowing the reaction blend to react for at least 1 hour;
(d) Optionally isolating a composition according to the first aspect.

N-methyl-glucamine, octanoic acid and decanoic acid are all available from Sigma-Aldrich.

"Reaction blend" is to be understood as a mixture of starting materials and optionally any solvents or other materials employed in or useful for the reaction. In at least one embodiment, the N-methyl-glucamine is added as an aqueous solution. In at least one embodiment, the reaction blend in step (a) comprises water.

In at least one embodiment, the heating in step (b) occurs by heating the reaction mixture to at least 100° C., more preferably at least 110° C., even more preferably at least 115° C., even more preferably from 120° C. to 150° C.

In at least one embodiment, the heating in step (b) occurs under vacuum. In at least one embodiment, the vacuum conditions are at least 20 mbar pressure.

In at least one embodiment, the step (c) occurs for at least 2 hours, more preferably at least 3 hours, even more preferably at least 4 hours, most preferably at least 6 hours.

In at least one embodiment, the step (c) occurs at at least 100° C., more preferably at least 110° C., even more preferably at least 115° C., even more preferably from 120° C. to 180° C., most preferably from 140° C. to 170° C.

In at least one embodiment, the step (c) occurs with stirring and under nitrogen gas.

During the synthesis process, a number of by-products may be formed. Examples include, for example, a compound according to Formula (2):

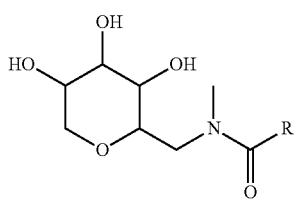
(2)

wherein R is a saturated or unsaturated hydrocarbon chain having seven or nine carbon atoms, or a mixture thereof. Another example of a by-product is a compound according to Formula (3):

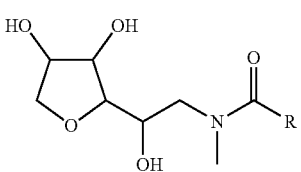
(3)

wherein R is a saturated or unsaturated hydrocarbon chain having seven or nine carbon atoms, or a mixture thereof. The compounds according to Formulae (2) and (3) are typically generated in the process at low levels e.g. less than 10 wt.-% by total weight of the composition. The compounds according to Formulae (2) and (3) may also have anti-microbial activity.

Other by-products that may be generated include: fatty esters of N-methyl cyclic glucamine; linear fatty N-methyl-glucamides; linear fatty N-methyl-diglucamides (i.e. two glucose moieties as the polar head group).

Example Embodiments of the Second Aspect:

In at least one embodiment, the second aspect relates to a process for synthesising the composition according to the first aspect comprising:
(a) Providing a hot melt of N-methyl-glucamine at a temperature of at least 100° C.;
(b) Contacting the hot melt of N-methyl-glucamine with octanoic acid, decanoic acid or a mixture thereof, to form a reaction blend;
(c) Heating the reaction blend to evaporate off any water, preferably by heating the reaction blend to at least 100° C., more preferably at least 110° C., even more preferably at least 115° C., even more preferably from 120° C. to 150° C.;
(d) Allowing the reaction blend to react for at least 1 hour, preferably for at least 2 hours, more preferably at least 3 hours, even more preferably at least 4 hours, most preferably at least 6 hours;
(e) Optionally isolating a composition according to the first aspect.

In at least one embodiment, the process comprises:
(a) Providing an aqueous solution of N-methyl-glucamine;
(b) Creating a hot melt of N-methyl-glucamine at a temperature of at least 100° C. by evaporating off the water from the aqueous solution of N-methyl-glucamine;
(c) Contacting the hot melt of N-methyl-glucamine with octanoic acid, decanoic acid or a mixture thereof, to form a reaction blend;
(d) Heating the reaction blend to at least 100° C., preferably at least 110° C., even more preferably at least 115° C., even more preferably from 120° C. to 150° C.;
(e) Allowing the reaction blend to react for at least 1 hour, preferably at least 2 hours, more preferably at least 3 hours;
(f) Optionally isolating a composition according to the first aspect.

In at least one embodiment, the process comprises:
(a) Providing an aqueous solution of N-methyl-glucamine;
(b) Creating a hot melt of N-methyl-glucamine at a temperature of at least 100° C. by evaporating off the water from the aqueous solution of N-methyl-glucamine;
(c) Contacting the hot melt of N-methyl-glucamine with octanoic acid, decanoic acid or a mixture thereof, to form a reaction blend, wherein the contacting occurs at a temperature of at least 100° C., preferably at least 110° C., even more preferably at least 115° C., even more preferably from 120° C. to 150° C.;
(d) Allowing the reaction blend to react for at least 1 hour, preferably at least 2 hours, more preferably at least 3 hours; and at a temperature of at least 100° C., preferably at least 110° C., even more preferably at least 115° C., even more preferably from 120° C. to 150° C.; and with stirring and under nitrogen gas;
(e) Optionally isolating a composition according to the first aspect.

Third Aspect

A third aspect relates to a preservative concentrate comprising:
compound X, wherein the compound X is according to Formula (I):

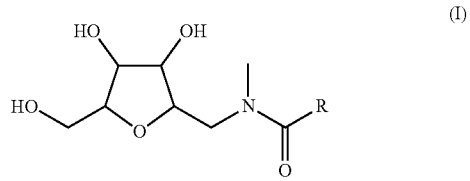
(I)

wherein R is a saturated or unsaturated hydrocarbon chain having seven or nine carbon atoms, or a mixture thereof; and
an anti-microbial active.

In at least one embodiment, compound X is a mixture of compounds according to Formula (I) wherein R is —(CH$_2$)$_8$CH$_3$ or —(CH$_2$)$_6$CH$_3$.

In at least one embodiment, the concentrate comprises from 1 wt.-% to 99 wt.-%, or from 5 wt.-% to 90 wt.-%, or from 5 wt.-% to 95 wt.-%, or from 20 wt.-% to 80 wt.-%, or from 30 wt.-% to 80 wt.-% compound X.

In at least one embodiment, the concentrate comprises from 1 wt.-% to 99 wt.-%, or from or from 5 wt.-% to 95 wt.-%, 10 wt.-% to 95 wt.-%, or from 20 wt.-% to 80 wt.-%, or from 20 wt.-% to 70 wt.-% anti-microbial active.

In at least one embodiment, the weight ratio of the compound X to the anti-microbial active is from 1:9 to 9:1.

In at least one embodiment, the anti-microbial active is selected from the group consisting of: aromatic alcohols, organic acids and salts thereof, compounds according to Formula (P), alkyl diols, halogenated compounds, isothiazolinones, preservation boosters and combinations thereof; wherein Formula (P) is as follows:

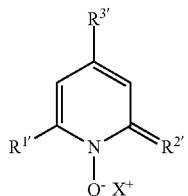

(P)

wherein
$R^{1'}$ is independently selected from H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;
$R^{2'}$ is either O or S,
$R^{3'}$ is H or a C1-C4-alkyl radical;
$X^+$ is a cation.
Preferably $R^{3'}$ is methyl.

In at least one embodiment, the aromatic alcohols are selected from the group consisting of benzyl alcohol, phenoxyethanol, veratryl alcohol, propylene phenoxyethanol, phenethyl alcohol, phenylpropanol, vanillin, 2-methyl-1-phenyl-2-propanol and combinations thereof.

In at least one embodiment, the organic acids and salts thereof are selected from the group consisting of benzoic acid, sorbic acid, dehydroacetic acid, lactic acid, salicylic acid, p-anisic acid, undecylenic acid, glycolic acid, propionic acid, and combinations thereof.

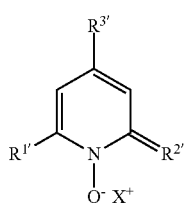

(P)

In at least one embodiment, the compound according to Formula (P) is selected from the group consisting of 2-hydroxypyridine-N-oxide, 2-pyridinthiol-1-oxide and salts thereof, 1-hydroxy-4-methyl-6-(2,4,4-trimethylpentyl)-2(1H)-pyridone and salts thereof (preferably the monoethanolamine salt), and combinations thereof. Formula (P) discloses and encompasses the tautomeric equivalents of these compounds since an equilibrium always exists. In at least one embodiment, the compound according to Formula (P) is Octopirox.

In at least one embodiment, the alkyl diols are selected from the group consisting of 1,2-pentanediol, 1,2-hexanediol, 1,6-hexanediol, 1,2-octanediol, 1,2-decanediol, methylpropanediol, and combinations thereof.

In at least one embodiment, the halogenated compounds are selected from the group consisting of chlorhexidine and salts thereof, triclosan, chlorphenesin, trichlorcarban, chloroxylenol, iodoproprinyl butylcarbamate, Bonopol, climbazole, and combinations thereof.

In at least one embodiment, the isothiazolinones are selected from the group consisting of methylisothiazolinone, methylchloroisothiazolinone, benzylisothiazolinone and combinations thereof.

In at least one embodiment, the preservation booster is selected from the group consisting of ethylhexylglycerol, sorbitan caprylate, isosorbide caprylate, glyceryl caprylate, glyceryl undecylenate, and combinations thereof.

In at least one embodiment, the preservation booster is ethylhexylglycerol.

In at least one embodiment, the anti-microbial active is selected from preservation boosters and preservatives.

In at least one embodiment, the preservative is selected from the group consisting of aromatic alcohols, organic acids and salts thereof, hydroxypyridones, alkyl diols, halogenated compounds, isothiazolinones and combinations thereof.

In at least one embodiment, the preservative is selected from the group consisting of hydroxy-4-methyl-6-(2,4,4-trimethylpentyl)-2(1H)-pyridone, benzoic acid, phenetyl alcohol, benzyl alcohol, phenoxyethanol, salts thereof, and combinations thereof.

In at least one embodiment, the preservative concentrate comprises:

compound X, wherein the compound X is according to Formula (I):

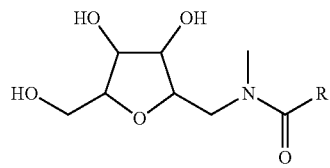

(I)

wherein R is a saturated or unsaturated hydrocarbon chain having seven or nine carbon atoms, or a mixture thereof; and
at least one preservation booster; and
at least one preservative, wherein the preservative is preferably selected from the group consisting of aromatic alcohols, organic acids and salts thereof, hydroxypyridones, alkyl diols, halogenated compounds, isothiazolinones and combinations thereof.

Preferably the preservation booster is selected from the group consisting of ethylhexylglycerol, sorbitan caprylate, isosorbide caprylate, glyceryl caprylate, glyceryl undecylenate, and combinations thereof.

Preferably, the preservative concentrate comprises:
compound X, wherein the compound X is according to Formula (I):

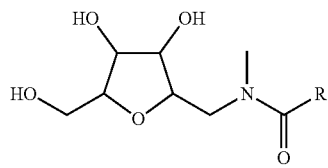

wherein R is a saturated or unsaturated hydrocarbon chain having seven or nine carbon atoms, or a mixture thereof; preferably wherein R is —(CH$_2$)$_8$CH$_3$ or —(CH$_2$)$_6$CH$_3$; and
sorbitan monocaprylate; and
benzyl alcohol.

In at least one embodiment, the concentrate is substantially free of a preservation booster.

In at least one embodiment, the concentrate is an aqueous solution.

In at least one embodiment, the concentrate comprises solvent. In at least one embodiment, the concentrate comprises a solvent, wherein the solvent comprises water and/or alcohol. Solvent is useful for providing the compounds used in present invention in liquid form. In at least one embodiment, the solvent is cosmetically acceptable. In at least one embodiment, the concentrate comprises at least 10 wt.-%, preferably at least 20 wt.-%, more preferably at least 30 wt.-%, even more preferably at least 50 wt.-% water. Water is useful for economic reasons but also because it is cosmetically acceptable. Optionally the concentrate comprises water-miscible or water-soluble solvents such as lower alkyl alcohols. In at least one embodiment, the concentrate comprises C$_1$-C$_5$ alkyl monohydric alcohols, preferably C$_2$-C$_3$ alkyl alcohols. The alcohols which may be present are in particular lower monohydric or polyhydric alcohols having 1 to 4 carbon atoms customarily used for cosmetic purposes, such as preferably ethanol and isopropanol.

Optionally, the concentrate comprises a water-soluble polyhydric alcohol. In at least one embodiment, the water-soluble polyhydric alcohols are polyhydric alcohols having two or more hydroxyl groups in the molecule. In at least one embodiment, the water-soluble polyhydric alcohol is selected from the group consisting of: dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether, and mixtures thereof.

In a preferred embodiment, the concentrate comprises a solvent selected from the group consisting of water, glycols, ethanol, and combinations thereof.

In a preferred embodiment, the concentrate comprises an aqueous, alcoholic or aqueous-alcoholic solvent, and wherein the aqueous, alcoholic or aqueous-alcoholic solvent comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof; more preferably wherein the aqueous, alcoholic or aqueous-alcoholic solvent comprises water, isopropanol, 1,2-propylene glycol, 1,3-propylene glycol, or mixtures thereof; even more preferably wherein the aqueous, alcoholic or aqueous-alcoholic solvent consists of water or consists of a mixture of water and an alcohol wherein the alcohol is selected from the group consisting of isopropanol, 1,2-propylene glycol and 1,3-propylene glycol.

Natural solvents can also be used. In at least one embodiment, the concentrate comprises a solvent selected from the group consisting of plant oil, honey, plant-derived sugar compositions, and mixtures thereof.

In at least one embodiment, the concentrate comprises additives common in cosmetology, pharmacy, and dermatology, which are hereinafter called auxiliaries. In at least one embodiment, the auxiliary is selected from the group consisting of oily substances, emulsifiers, coemulsifiers, cationic polymers, film formers, superfatting agents, stabilizers, active biogenic substances, glycerol, preservatives, pearlizing agents, dyes and fragrances, solvents, opacifiers, functional acids, and also protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and/or carriers/solvents. Preferably the auxiliary is selected from the group consisting of oily substances, emulsifiers, coemulsifiers, cationic polymers, film formers, superfatting agents, stabilizers, active biogenic substances, glycerol, pearlizing agents, dyes, fragrances, opacifiers, functional acids, protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and combinations thereof.

In at least one embodiment, the concentrate comprises water soluble vitamins and their derivatives, water soluble amino acids and their salts and/or derivatives, viscosity modifiers, dyes, nonvolatile solvents or diluents (water soluble and insoluble), pearlescent aids, thickeners, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine, minoxidil, and combinations thereof. In at least one embodiment, the concentrate comprises from 0 wt.-% to 5 wt.-% vitamins and amino acids, by total weight of the concentrate. The concentrate may also comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The concentrate may comprise from 0 wt.-%, preferably from 0.0001 wt.-% to 5 wt.-% pigment materials.

Example Embodiments of the Third Aspect:

In at least one embodiment, the third aspect relates to a preservative concentrate consisting of:

compound X, wherein the compound X is according to Formula (I):

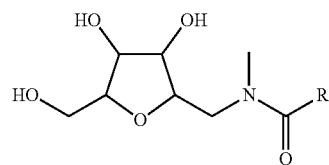

(I)

wherein R is a saturated or unsaturated hydrocarbon chain having seven or nine carbon atoms, or a mixture thereof; and an anti-microbial active;

optionally a solvent;

optionally an auxiliary, wherein the auxiliary is selected from the group consisting of oily substances, emulsifiers, coemulsifiers, cationic polymers, film formers, superfatting agents, stabilizers, active biogenic substances, glycerol, pearlizing agents, dyes, fragrances, opacifiers, functional acids, protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and combinations thereof.

In at least one embodiment, the third aspect relates to a preservative concentrate consisting of:

at least 15 wt.-% of a compound X, wherein the compound X is according to Formula (I)

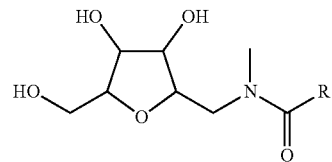

(I)

wherein compound X is a mixture of compounds according to Formula (I)

wherein R is —(CH$_2$)$_8$CH$_3$ or —(CH$_2$)$_6$CH$_3$; and at least 10 wt.-% of an anti-microbial active;

optionally at least 75 wt.-% solvent;

optionally an auxiliary, wherein the auxiliary is selected from the group consisting of oily substances, emulsifiers, coemulsifiers, cationic polymers, film formers, superfatting agents, stabilizers, active biogenic substances, glycerol, pearlizing agents, dyes, fragrances, opacifiers, functional acids, protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and combinations thereof.

In at least one embodiment, the third aspect relates to a preservative concentrate consisting of:

at least 15 wt.-% of a compound X, wherein the compound X is according to Formula (I)

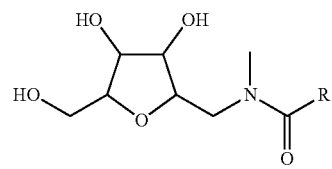

(I)

wherein compound X is a mixture of compounds according to Formula (I)

wherein R is —(CH$_2$)$_8$CH$_3$ or —(CH$_2$)$_6$CH$_3$; and a preservative, wherein the preservative is selected from the group consisting of hydroxy-4-methyl-6-(2,4,4-trimethylpentyl)-2(1H)-pyridone, benzoic acid, phenetyl alcohol, benzyl alcohol, phenoxyethanol, salts thereof, and combinations thereof;

optionally a solvent;

optionally an auxiliary, wherein the auxiliary is selected from the group consisting of oily substances, emulsifiers, coemulsifiers, cationic polymers, film formers, superfatting agents, stabilizers, active biogenic substances, glycerol, pearlizing agents, dyes, fragrances, opacifiers, functional acids, protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and combinations thereof.

In at least one embodiment, the third aspect relates to a preservative concentrate consisting of:

at least 15 wt.-% of a compound X, wherein the compound X is according to Formula (I)

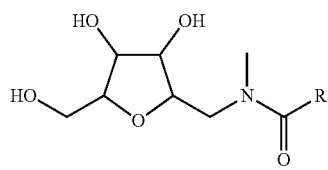

wherein compound X is a mixture of compounds according to Formula (I)
wherein R is —(CH$_2$)$_8$CH$_3$ or —(CH$_2$)$_6$CH$_3$; and
at least 10 wt.-% a preservative, wherein the preservative is selected from the group consisting of hydroxy-4-methyl-6-(2,4,4-trimethylpentyl)-2(1H)-pyridone, benzoic acid, phenetyl alcohol, benzyl alcohol, phenoxyethanol, salts thereof, and combinations thereof;
optionally a solvent;
optionally an auxiliary, wherein the auxiliary is selected from the group consisting of oily substances, emulsifiers, coemulsifiers, cationic polymers, film formers, superfatting agents, stabilizers, active biogenic substances, glycerol, pearlizing agents, dyes, fragrances, opacifiers, functional acids, protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and combinations thereof.

Fourth Aspect

A fourth aspect relates to the use of a compound X as a preservative booster or as an antimicrobial agent, wherein compound X is according to Formula (I):

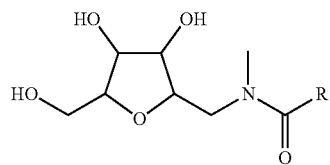

wherein R is a saturated or unsaturated hydrocarbon chain having seven or nine carbon atoms, or a mixture thereof. Preferably compound X is a mixture of compounds according to Formula (I) wherein R is —(CH$_2$)$_8$CH$_3$ or —(CH$_2$)$_6$CH$_3$.

At least one embodiment relates to the use of a compound X as an antifungal agent, wherein compound X is according to Formula (I):

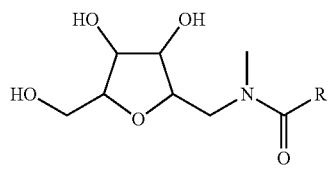

wherein R is a saturated or unsaturated hydrocarbon chain having seven or nine carbon atoms, or a mixture thereof. Preferably compound X is a mixture of compounds according to Formula (I) wherein R is —(CH$_2$)$_8$CH$_3$ or —(CH$_2$)$_6$CH$_3$.

An alternative embodiment of the fourth aspect relates to the use of a compound X as an emulsifier or solubiliser, wherein compound X is according to Formula (I):

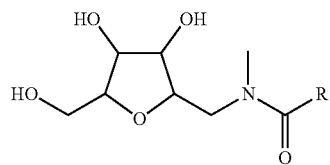

wherein R is a saturated or unsaturated hydrocarbon chain having seven or nine carbon atoms, or a mixture thereof. Preferably compound X is a mixture of compounds according to Formula (I) wherein R is —(CH$_2$)$_8$CH$_3$ or —(CH$_2$)$_6$CH$_3$.

Fifth Aspect

A fifth aspect relates to a method of reducing the effects of micro-organisms, wherein the method comprises adding the composition according to the first aspect to an antimicrobial active to form a formulation. In at least one embodiment, the formulation is according to the sixth aspect.

In at least one embodiment, the level of the composition added to the formulation is from 0.001 wt.-% to 20 wt.-%, preferably 0.01 wt.-% to 10 wt.-%, more preferably 0.1 wt.-% to 5 wt.-%, by total weight of the formulation.

Sixth Aspect

A sixth aspect relates to a formulation comprising a compound X according to Formula (I)

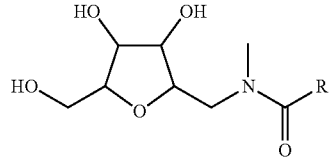

wherein R is a saturated or unsaturated hydrocarbon chain having seven or nine carbon atoms, or a mixture thereof. In at least one embodiment, the formulation comprises from 0.001 wt.-% to 20 wt.-%, preferably 0.01 wt.-% to 10 wt.-%, more preferably 0.1 wt.-% to 5 wt.-% compound X, by total weight of the formulation. Preferably compound X is a mixture of compounds according to Formula (I) wherein R is —(CH$_2$)$_8$CH$_3$ or —(CH$_2$)$_6$CH$_3$.

In at least one embodiment, the formulation comprises the composition according to the first aspect and/or the concentrate according to the third aspect.

In at least one embodiment, the formulation is selected from the group consisting of cosmetic formulations and household cleansing formulations.

In at least one embodiment, the formulation is a formulation selected from the group consisting of shampoo, body wash, facial cleanser, cleansing masks, bubble bath, bath oil, cleansing milk, micellar water, make-up remover, cleansing wipes, perfume, soaps, shaving soaps, shaving foams and cleansing foams.

In at least one embodiment, the formulation is a cosmetic formulation for cleansing hair and/or skin.

In at least one embodiment, the formulation is an aqueous solution.

In at least one embodiment, the formulation comprises solvent. In at least one embodiment, the formulation comprises a solvent, wherein the solvent comprises water and/or alcohol. Solvent is useful for providing the compounds used in present invention in liquid form. In at least one embodiment, the solvent is cosmetically acceptable. In at least one embodiment, the formulation comprises at least 10 wt.-%, preferably at least 20 wt.-%, more preferably at least 30 wt.-%, even more preferably at least 50 wt.-% water. Water is useful for economic reasons but also because it is cosmetically acceptable. Optionally the formulation comprises water-miscible or water-soluble solvents such as lower alkyl alcohols. In at least one embodiment, the formulation comprises $C_1$-$C_5$ alkyl monohydric alcohols, preferably $C_2$-$C_3$ alkyl alcohols. The alcohols which may be present are in particular lower monohydric or polyhydric alcohols having 1 to 4 carbon atoms customarily used for cosmetic purposes, such as preferably ethanol and isopropanol.

Optionally, the formulation comprises a water-soluble polyhydric alcohol. In at least one embodiment, the water-soluble polyhydric alcohols are polyhydric alcohols having two or more hydroxyl groups in the molecule. In at least one embodiment, the water-soluble polyhydric alcohol is selected from the group consisting of: dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether, and mixtures thereof.

In a preferred embodiment, the formulation comprises a solvent selected from the group consisting of water, glycols, ethanol, and combinations thereof.

In a preferred embodiment, the formulation comprises an aqueous, alcoholic or aqueous-alcoholic solvent, and wherein the aqueous, alcoholic or aqueous-alcoholic solvent comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof; more preferably wherein the aqueous, alcoholic or aqueous-alcoholic solvent comprises water, isopropanol, 1,2-propylene glycol, 1,3-propylene glycol, or mixtures thereof;

even more preferably wherein the aqueous, alcoholic or aqueous-alcoholic solvent consists of water or consists of a mixture of water and an alcohol wherein the alcohol is selected from the group consisting of isopropanol, 1,2-propylene glycol and 1,3-propylene glycol.

Natural solvents can also be used. In at least one embodiment, the formulation comprises a solvent selected from the group consisting of plant oil, honey, plant-derived sugar compositions, and mixtures thereof.

In at least one embodiment, the formulation comprises additives common in cosmetology, pharmacy, and dermatology, which are hereinafter called auxiliaries. In at least one embodiment, the auxiliary is selected from the group consisting of oily substances, emulsifiers, coemulsifiers, cationic polymers, film formers, superfatting agents, stabilizers, active biogenic substances, glycerol, preservatives, pearlizing agents, dyes and fragrances, solvents, opacifiers, functional acids, and also protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and/or carriers/solvents.

In at least one embodiment, the formulation comprises water soluble vitamins and their derivatives, water soluble amino acids and their salts and/or derivatives, viscosity modifiers, dyes, nonvolatile solvents or diluents (water soluble and insoluble), pearlescent aids, thickeners, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine, minoxidil, and combinations thereof. In at least one embodiment, the formulation comprises from 0 wt.-% to 5 wt.-% vitamins and amino acids, by total weight of the formulation. The formulation may also comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I.

Names. The formulation may comprise from 0 wt.-%, preferably from 0.0001 wt.-% to 5 wt.-% pigment materials.

In at least one embodiment, the formulation comprises an oily substance, which is any fatty substance which is liquid at room temperature (25° C.). In at least one embodiment, the formulation comprises oily substance selected from the group consisting of silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, argan oil, abyssinian oil, and coconut oil; synthetic oils such as purcellin oil, isoparaffins, linear and/or branched fatty alcohols and fatty acid esters, preferably guerbet alcohols having 6 to 18, preferably 8 to 10, carbon atoms; esters of linear (C6-013) fatty acids with linear ($C_6$-$C_{20}$) fatty alcohols; esters of branched (C6-$C_{13}$) carboxylic acids with linear ($C_6$-$C_{20}$) fatty alcohols, esters of linear (C6-$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$-$C_{10}$) fatty acids; esters such as dioctyl adipate, diisopropyl dimer dilinoleate; propylene glycols/dicaprylate or waxes such as beeswax, paraffin wax or microwaxes, alone or in combination with hydrophilic waxes, such as cetyl-stearyl alcohol, for example; fluorinated and perfluorinated oils; fluorinated silicone oils; mixtures of the aforementioned compounds.

In at least one embodiment, the formulation comprises a non-ionic coemulsifier. In at least one embodiment, the non-ionic coemulsifier is selected from adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; (C12-C18) fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from one or more of these classes of substance. Examples of suitable ionogenic coemulsifiers include anionic emulsifiers, such as mono-, di- or tri-phosphoric esters, but also cationic emulsifiers such as mono-, di-, and tri-alkyl quats and their polymeric derivatives.

In at least one embodiment, the formulation comprises a cationic polymer. Suitable cationic polymers include those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37 & mineral oil & PPG trideceth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylam ides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

In at least one embodiment, the formulation comprises a superfatting agent. As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

In at least one embodiment, the formulation comprises a stabiliser. As stabiliser it is possible to use metal salts of fatty acids, such as magnesium, aluminum and/or zinc stearate, for example.

In at least one embodiment, the formulation comprises a care additive. The formulations can be blended with conventional ceram ides, pseudoceram ides, fatty acid N-alkylpolyhydroxyalkyl amides, cholesterol, cholesterol fatty acid esters, fatty acids, triglycerides, cerebrosides, phospholipids, panthenol and similar substances as a care additive.

In at least one embodiment, the formulation comprises an anti-fungal substance. In at least one embodiment, the anti-fungal substance is selected from the group consisting of ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, zinc pyrithione, octopirox, and combinations thereof. In at least one embodiment, the formulation comprises a total amount of anti-fungal substance in the formulation of from 0.1 wt.-% to 1 wt.-%. In at least one embodiment, the formulation comprises a pyridinethione anti-dandruff particulates, for example 1-hydroxy-2-pyridinethione salts, are highly preferred particulate anti-dandruff agents. The concentration of pyridinethione antidandruff particulate may ranges from 0.1 wt.-% to 4 wt.-%, by total weight of the formulation, preferably from 0.1 wt.-% to 3 wt.-%, more preferably from 0.3 wt.-% to 2 wt.-%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form. Salts formed from other cations, such as sodium, may also be suitable. Pyridinethione anti-dandruff agents are described, for example, in U.S. Pat. Nos. 2,809,971; 3,236,733; 3,753,196; 3,761, 418; 4,345,080; 4,323,683;

U.S. Pat. Nos. 4,379,753; and 4,470,982. It is contemplated that when ZPT is used as the anti-dandruff particulate in the formulations herein, that the growth or regrowth of hair may be stimulated or regulated, or both, or that hair loss may be reduced or inhibited, or that hair may appear thicker or fuller.

Functional acids are acidic substances used to impart a clinical functionality to the skin or hair upon application. Suitable functional acids include alpha hydroxy acids, beta-hydroxy acids, lactic acid, retinoic acid, and similar substances.

In at least one embodiment, the formulation comprises an astringent. In at least one embodiment, the astringent is selected from the group consisting of magnesium oxide, aluminium oxide, titanium dioxide, zirconium dioxide, zinc oxide, oxide hydrates, aluminium oxide hydrate (boehmite) and hydroxide, chlorohydrates of calcium, magnesium, aluminium, titanium, zirconium or zinc. In at least one embodiment, the formulation comprises from 0.001 wt.-% to 10 wt.-%, or from 0.01 wt.-% to 9 wt.-%, or from 0.05 wt.-% to 8 wt.-%, or from 0.1 wt.-% to 5 wt.-% astringent.

In at least one embodiment, the formulation comprises a deodorising agent. In at least one embodiment, the deodorising agent is selected from the group consisting of allantoin, bisabolol, and combinations thereof. In at least one embodiment, the formulation comprises from 0.001 wt.-% to 10 wt.-%, or from 0.01 wt.-% to 9 wt.-%, or from 0.05 wt.-% to 8 wt.-%, or from 0.1 wt.-% to 5 wt.-% deodorising agent.

In at least one embodiment, the formulation comprises a sun protection agent and/or UV filter. Suitable sun protection agents and UV filters are disclosed in WO-2013/017262A1 (published on 7 Feb. 2013), from page 32, line 11 to the end of page 33. In at least one embodiment, the sun protection agent and/or UV filter is selected from the group consisting of 4-amino benzoic acid, 3-(4'-trimethylammonium)-benzylide-boran-2-one-methylsulfate, camphor benzalkonium methosulfate, 3,3,5-trimethyl-cyclohexylsalicylate, 2-hydroxy-4-methoxybenzophenone, 2-phenylbenzimidazole-5-sulfonic acid and potassium-, sodium- and triethanolamine salts thereof, 3,3'-(1,4-phenylene dimethine)-bis-(7,7-dimethyl-2-oxobicyclo[2.2.1]-heptane-1-methane sulfonic acid) and its salts, 1-(4-tert.-butylphenyl)-3-(4-methoxyphenyl) propan-1,3-dion, 3-(4'-sulfo)-benzylidene-bornane-2-one its salts, 2-cyan-3,3-diphenyl-acrylic acid-(2-ethylhexylester), polymers of N-[2(and 4)-(2-oxoborn-3-ylidenmethyl)benzyl]-acrylamide, 4-methoxy-cinnamic acid-2-ethyl-hexylester, ethoxylated ethyl-4-amino-benzoate, 4-methoxy-cinnamic acid-isoamylester, 2,4,6-tris-[p-(2-ethylhexyloxycarbonyl)anilino]-1,3,5-triazine, 2-(2H-benzotriazole-2-yl)-4-methyl-6-(2-methyl-3-(1,3,3,3-tetramethyl-1-(trimethylsilyloxy)-disiloxanyl)-propyl) phenol, 4,4'-[(6-[4-((1,1-dimethylethyl)-amino-carbonyl) phenylamino]-1,3,5-triazin-2,4-yl)diimino]bis-(benzoic acid-2-ethylhexylester), 3-benzophenone, 4-benzophenone (acic), 3(4'-methylbenzyliden)-D,L-camphor, 3-benzylidene-camphor, salicylic acid-2-ethylhexylester, 4-dimethyl aminobenzic acid-2-ethylhexylester, hydroxy-4-methoxy-benzophenone-5 sulfonic acid and the sodium salt thereof, 4-isopropyl benzylsalicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and its sodium, potassium, and triethanolamine salts, octylmethoxy cinnamic acid, isopentyl-4-methoxy cinnamic acid, isoamyl-p-methoxy cinnamic acid, 2,4,6-trianilino-(p-carbo-2'-ethylhexyl-1'-oxy)-1,3,5-triazine (octyl triazone) phenol, 2,2(2H-benzotriazol-2-yl)-4-methyl-6-(2-methyl-3-(1,3,3,3-tetramethyl-1-(trimethylsilyl)oxy)-disiloxanyl)propyl (drometrizole trisiloxane) benzic acid, 4,44 (6-(((1,1-dimethylethyl)amino)carbonyl)phenyl)amino)-1,3,5-triazine-2,4-diyl)diimino)bis,bis(2-ethylhexyl)ester) benzoic acid, 4,4-((6-(((1,1-dimethylethyl)amino)-carbonyl) phenyl)amino)-1,3,5-triazine-2,4-diyl)diimino)bis,bis(2-ethylhexyl)ester), 3-(4'-methylbenzylidene)-D,L-camphor (4-methylbenzylidene camphor), benzylidene-camphor-sulfonic acid, octocrylene, polyacrylamidomethyl-benzylidene-camphor, 2-ethylhexyl salicylate (octyl salicylate), 4-dimethyl-aminobenzoeacidethyl-2-hexylester (octyl dimethyl PABA), PEG-25 PABA, 2 hydroxy-4-methoxybenzophenone-5-sulfonic acid (5-benzophenone) and the sodium salt thereof, 2,2'-methylene-bis-6-(2H-benzotriazol-2-yl)-4-(tetramethyl-butyl)-1,1,3,3-phenol, the sodium salt of 2-2'-bis-(1,4-phenylene)1H-benzimidazole-4,6-disulfonic acid, (1,3,5)-triazine-2,4-bis((4-(2-ethyl-hexyloxy)-2-hydroxy)-phenyl)-6-(4-methoxyphenyl), 2-ethylhexyl-2-cyano-3,3-diphenyl-2-propenoate, glyceryl octanoate, di-p-methoxy cinnamic acid, p-amino-benzoic acid and its ester, 4-tert-butyl-4'-methoxydibenzoylmethane, 4-(2-β-glucopyranoxy) propoxy-2-hydroxybenzophenone, octyl salicylate, methyl-2,5-diisopropyl cinnamic acid, cinoxate, dihydroxy-dimethoxybenzophenone, disodium salts of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl-dimethoxybenzyliden-dioxoimidazolidinpropionate, methylene-bis-benztriazolyl tetramethylbutylphenol, phenyldibenzimidazoltetrasulfonate, bis-ethylhexyloxyphenol-methoxyphenol-triazine, tetrahydroxybenzophenone, terephthalylidendicamphor-sulfonic acid, 2,4,6-tris[4,2-ethylhexyloxycarbonyl)anilino]-1,3,5-triazine, methyl-bis(trimethylsiloxy)silyl-isopentyl trimethoxy cinnamic acid, amyl-p-dimethylaminobenzoate, amyl-p-dimethylamino benzoate, 2-ethylhexyl-p-dimethylaminobenzoate, isopropyl-p-methoxy cinnamic acid/diisopropyl cinnamic acid ester, 2-ethylhexyl-p-methoxy cinnamic acid, 2-hydroxy-4-methoxy benzophenone, 2-hydroxy-4-methoxybenzophenone-5-sulfonic acid and the trihydrate, 2-hydroxy-4-methoxybenzophenone-5-sulfonate sodium salt, phenylbenzimidazole sulfonic acid, and combinations thereof. In at least one embodiment, the formulation comprises from 0.001 wt.-% to 10 wt.-%, preferably from 0.05 wt.-% to 5 wt.-%, even more preferably from 0.1 wt.-% to 3 wt.-%, most preferably from 0.05 wt.-% to 1 wt.-% sun protection agent and/or UV filter. In at least one embodiment, the formulation comprises a photoprotective substance in an amount of from 0.01 to 10 wt.-%, or from 0.1 to 5 wt.-%, more preferably from 0.2 to 2 wt.-%. Suitable photoprotective substances include, in particular, all of the photoprotective substances specified in EP1084696A1 (L'OREAL), which is incorporated herein by reference. In a preferred embodiment, the photoprotective substance is selected from the group consisting of 2-ethylhexyl 4-methoxycinnamate, methyl methoxycinnamate, 2-hydroxy-4-methoxybenzophenone-5-sulfonic acid, polyethoxylated p-aminobenzoates, and combinations thereof.

In at least one embodiment, the formulation comprises an anti-oxidant. In at least one embodiment, the anti-oxidant is selected from the group consisting of amino acids, peptides, sugars, imidazoles, carotinoids, carotenes, chlorogenic acid, lipoic acid, thiols, thiol glycosyl esters, thiol N-acetyl esters, thiol methyl esters, thiol ethyl esters, thiol propyl esters, thiol amyl esters, thiol butyl esters, thiol lauryl esters, thiol palmitoyl esters, thiol oleyl esters, thiol linoleyl esters, thiol cholesteryl esters, thiol glyceryl esters, dilaurylthiodipropionate, distearylthiodipropionate, thiodipropionic acid, metal chelators, hydroxy acids, fatty acids, folic acids, vitamin C, tocopherol, vitamin A, stilbenes, derivatives and combinations thereof. In at least one embodiment, the anti-oxidant is selected from the group consisting of glycine, histidine, tyrosine, tryptophan, urocaninic acid, D,L-carnosine, D-carnosine, L-carnosine, beta-carotene, alpha-carotene, lycopene, dihydrolipoic acid, aurothioglucose, propylthiouracil, thioredoxine, glutathione, cysteine, cystine, cystamine, buthioninsulfoximine, homocysteinsulfoximine, buthioninsulfone, penta-, hexa-, heptathioninsulfoximine, hydroxyfatty acids, palmitic acid, phytinic acid, lactoferrin, citric acid, lactic acid, malic acid, humic acid, bile acid, bilirubin, biliverdin, EDTA, EGTA, linoleic acid, linolenic acid, oleic acid, butylhydroxyanisol, trihydroxybutyrophenone, ubichinon, ubichinol, ascorbylpalmitate, Mg-ascorbylphosphate, ascorbylacetate, vitamin E acetate, vitamin A palmitate, carnosine, mannose, ZnO, ZnSO$_4$, selenium methionine, stilbenes, superoxide dismutase, and combinations thereof. In at least one embodiment, the antioxidant is selected from the group consisting of vitamin A, vitamin A derivatives, vitamin E, vitamin E derivatives, and combinations thereof. In at least one embodiment, the formulation comprises from 0.001 wt.-% to 10 wt.-%, preferably from 0.05 wt.-% to 5 wt.-%, even more preferably from 0.1 wt.-% to 3 wt.-%, most preferably from 0.05 wt.-% to 1 wt.-% antioxidant.

In at least one embodiment, the formulation comprises a dye or pigment. In at least one embodiment, the formulation comprises at least one pigment. Suitable dyes and pigments are disclosed in WO2013/017262A1 in the table spanning pages 36 to 43. These may be colored pigments which impart color effects to the product mass or to hair, or they may be luster effect pigments which impart luster effects to the product mass or to the hair. The color or luster effects on the hair are preferably temporary, i.e. they last until the next hair wash and can be removed again by washing the hair with customary shampoos. In at least one embodiment, the formulation comprises a total amount of from 0.01 wt.-% to 25 wt.-%, preferably from 5 wt.-% to 15 wt.-% pigment. In at least one embodiment, the particle size of the pigment is from 1 micron to 200 micron, preferably from 3 micron to 150 micron, more preferably 10 micron to 100 micron. The pigments are colorants which are virtually insoluble in the application medium, and may be inorganic or organic. Inorganic-organic mixed pigments are also possible. Preference is given to inorganic pigments. The advantage of inorganic pigments is their excellent resistance to light, weather and temperature. The inorganic pigments may be of natural origin. In at least one embodiment, the inorganic pigment is selected from the group consisting of chalk, ochre, umber, green earth, burnt sienna, graphite, and combinations thereof. The pigments may be white pigments, such as, for example, titanium dioxide or zinc oxide, black pigments, such as, for example, iron oxide black, colored pigments, such as, for example, ultramarine or iron oxide red, lustre pigments, metal effect pigments, pearlescent pigments, and fluorescent or phosphorescent pigments, where preferably at least one pigment is a colored, nonwhite pigment. In at least one embodiment, the pigment is selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments), and combinations thereof. In at least one embodiment, the pigment is selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), and combinations thereof. In at least one embodiment, the pigment is selected from the group consisting of pearlescent and colored pigments based on mica which are coated with a metal oxide or a metal oxychloride, such as titanium dioxide or bismuth oxychloride, and optionally further color-imparting substances, such as iron oxides, Prussian blue, ultramarine, carmine etc. and where the color can be determined by varying the layer thickness. Such pigments are sold, for example, under the trade names Rona®, Colorona®, Dichrona® and Timiron® by Merck, Germany. In at least one embodiment, the pigment is selected from the group consisting of organic pigments such as sepia, gamboge, bone charcoal, Cassel brown, indigo, chlorophyll and other plant pigments. In at least one embodiment, the pigment is selected from the group consisting of synthetic organic pigments such as azo pigments, anthraquinoids, indigoids, dioxazine, quinacridone, phthalocyanine, isoindolinone, perylene and perinone, metal complex, alkali blue and diketopyrrolopyrrole pigments.

In at least one embodiment, the formulation comprises from 0.01 wt.-% to 10 wt.-%, preferably from 0.05 wt.-% to 5 wt.-%, of at least one particulate substance. Suitable substances are, for example, substances which are solid at room temperature (25° C.) and are in the form of particles. In at least one embodiment, the particulate substance is selected from the group consisting of silica, silicates, aluminates, clay earths, mica, insoluble salts, in particular insoluble inorganic metal salts, metal oxides, e.g. titanium dioxide, minerals and insoluble polymer particles are suitable. The particles may be present in the formulation in undissolved, preferably stably dispersed form, and, following application to the keratin substrate and evaporation of the solvent, can deposit on the substrate in solid form. A stable dispersion can be achieved by providing the formulation with a yield point which is large enough to prevent the solid particles from sinking. An adequate yield point can be established using suitable gel formers in a suitable amount. In at least one embodiment, the particulate substance is selected from the group consisting of silica (silica gel, silicon dioxide) and metal salts, in particular inorganic metal salts, where silica is particularly preferred. Metal salts are, for example, alkali metal or alkaline earth metal halides, such as sodium chloride or potassium chloride; alkali metal or alkaline earth metal sulfates, such as sodium sulfate or magnesium sulfate.

In at least one embodiment, the formulation comprises a direct dye. Preferred among the direct dyes are the following compounds, alone or in combination with one another: Hydroxyethyl-2-nitro-p-toluidine, 2-hydroxyethylpicramic acid, 4-nitrophenylaminourea, tri(4-amino-3-methylphenyl) carbenium chloride (Basic Violet 2), 1,4-di-amino-9,10-anthracenedione (Disperse Violet 1), 1-(2-hydroxy-ethyl)amino-2-nitro-4-[di(2-hydroxyethyl)amino]benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio) naphthalene chloride (C.I. 12245; Basic Red No. 76), 3-methyl-1-phenyl-4-{[3-(trimethylammonio)phenyl]azo}pyrazol-5-one chloride (C.I. 12719; Basic Yellow No. 57) and 2,6-diamino-3-[(pyridin-3-yl)azo]pyridine as well as the salts thereof. Particularly preferred among the aforesaid direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-di-amino-9,10-anthracenedione (Disperse Violet 1), 1-(2-hydroxy-ethyl)amino-2-nitro-4-[di(2-hydro-xyethyl)amino]benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)-amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (CA. 56059; Basic Blue No. 99), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio)naphthalene chloride (C.I. 12245; Basic Red No. 76), 3-methyl-1-phenyl-4-{[3-(trimethylammonio)phenyl]azo}pyrazol-5-one chloride (C.I. 12719; Basic Yellow No. 57) and 2,6-diamino-3-[(pyridin-3-yl)azo]pyridine as well as the salts thereof. In at least one embodiment, the total quantity of direct dyes in the formulation amounts to 0.01 to 15 wt.-%, preferably 0.1 to 10 wt.-%, most preferred 0.5 to 8 wt.-%.

In at least one embodiment, the formulation comprises a conditioning agent. In at least one embodiment, the conditioning agent is a water insoluble, water dispersible, non-volatile, liquid that forms emulsified, liquid particles. In at least one embodiment, the conditioning agent is a silicone (e.g., silicone oil, cationic silicone, silicone gum, high refractive silicone, and silicone resin), an organic conditioning oil (e.g., hydrocarbon oils, polyolefins, and fatty esters), a cationic conditioning surfactant, a high melting point fatty compound, or combinations thereof.

In at least one embodiment, the conditioning agent is a silicone, and wherein the formulation comprises from 0.01% to 10%, or from 0.1% to 5% silicone conditioning agent, by total weight of the formulation. Suitable silicone conditioning agents, and optional suspending agents for the silicone, are described in U.S. Pat. No. 5,104,646. In at least one embodiment, the formulation comprises a silicone gum selected from the group consisting of polydimethylsiloxane, (polydimethylsiloxane) (methylvinylsiloxane) copolymer, poly(dimethylsiloxane) (diphenylsiloxane) (methylvinylsiloxane) copolymer, and mixtures thereof.

In at least one embodiment, the formulation comprises a terminal aminosilicone. "Terminal aminosilicone" as defined herein means silicone comprising one or more amino groups at one or both ends of the silicone backbone. In at least one embodiment, the formulation is substantially free of any silicone compound comprising pendant amino groups. In an embodiment, the formulation is substantially free of any silicone compound other than terminal aminosilicones. In at least one embodiment, the amino group at least one terminus of the silicone backbone of the terminal aminosilicone is selected from the group consisting of primary amines, secondary amines and tertiary amines. In at least one embodiment, the formulation comprises a terminal aminosilicone conforming to Formula (S):

(S)

wherein

G is hydrogen, phenyl, hydroxy, or C1-C8 alkyl, preferably methyl;

a is an integer having a value from 1 to 3, preferably 1; b is 0, 1 or 2, preferably 1;

n is a number from 0 to 1,999;

$R^F$ is a monovalent radical conforming to the general formula $C_qH_{2q}L$, wherein q is an integer having a value from 2 to 8 and L is selected from the following groups: $—N(R^T)CH_2—CH_2—N(R^T)_2$; $—N(R^T)_2$; $—N(R^T)_3A^-$; $—N(R^T)CH_2—CH_2—NR^TH_2A^-$; wherein $R^T$ is hydrogen, phenyl, benzyl, or a saturated hydrocarbon radical, preferably an alkyl radical from having from 1 to 20 carbon atoms; $A^-$ is a halide ion.

In at least one embodiment, the terminal aminosilicone corresponding to Formula (S) has a=1, q=3, G=methyl, n is from 1000 to 2500, alternatively from 1500 to 1700; and L is $—N(CH_3)_2$. A suitable terminal aminosilicone corresponding to Formula (III) has a=0, G=methyl, n is from 100 to 1500, or from 200 to 800, and L is selected from the following groups: $—N(R^T)CH_2—CH_2—N(R^T)_2$; $—N(R^T)_2$; $—N(R^T)_3A^-$; $—N(R^T)CH_2—CH_2—NR^TH_2A^-$; wherein $R^T$ is hydrogen, phenyl, benzyl, or a saturated hydrocarbon radical, preferably an alkyl radical from having from 1 to 20 carbon atoms; $A^-$ is a halide ion, alternatively L is $—NH_2$. In at least one embodiment, the terminal aminosilicone is selected from the group consisting of bis-aminomethyl dimethicone, bisaminoethyl dimethicone, bis-aminopropyl dimethicone, bis-aminobutyl dimethicone, and mixtures thereof. In an embodiment, the viscosity of the terminal aminosilicone is from 1,000 to 30,000 cPs, or from 5,000 to 20,000 cPs measured at 25° C.

In at least one embodiment, the formulation comprises from 0.1% to 20%, or from 0.5% to 10%, or from 1% to 6% terminal aminosilicone, by total weight of the formulation.

In at least one embodiment, the formulation comprises a high melting point fatty compound. The high melting point fatty compound has a melting point of 25° C. or higher. In at least one embodiment, the high melting point fatty compound is selected from the group consisting of a fatty alcohol, fatty acid, fatty alcohol derivative, fatty acid derivative, and mixtures thereof. Non-limiting examples of the high melting point fatty compounds are found in International Cosmetic Ingredient Dictionary, Fifth Edition, 1993, and CTFA Cosmetic Ingredient Handbook, Second Edition, 1992. The formulation may comprise from 0.1% to 40%, or from 1% to 30%, or from 1.5% to 16%, or from 1.5% to 8% of a high melting point fatty compound, by total weight of the formulation. This is advantageous in view of providing improved conditioning benefits such as slippery feel during the application to wet hair, softness and moisturized feel on dry hair. In at least one embodiment, the fatty alcohol is selected from the group consisting of: cetyl alcohol, stearyl alcohol, behenyl alcohol, and mixtures thereof. In at least one embodiment, the formulation comprises a linear fatty alcohol, wherein the linear fatty alcohol is comprised in a lamellar gel matrix. A lamellar gel matrix is suitable for providing various conditioning benefits such as slippery feel during the application to wet hair and softness and moisturized feel on dry hair. The linear fatty alcohol may comprise from 8 to 24 carbon atoms. In an embodiment, the linear fatty alcohol is selected from the group consisting of: cetyl alcohol, stearyl alcohol, and mixtures thereof. In an embodiment, the weight ratio of total linear fatty alcohol to terminal aminosilicone is from 0.5:1 to 10:1, or from 1:1 to 5:1, or from 2.4:1 to 2.7:1.

In at least one embodiment, the lamellar gel matrix comprises a cationic conditioning surfactant and a high melting point fatty compound. In view of providing the lamellar gel matrix, the cationic conditioning surfactant and the high melting point fatty compound are contained at a level such that the weight ratio of the cationic surfactant to the high melting point fatty compound is in the range of from 1:1 to 1:10, or from 1:1 to 1:6.

In at least one embodiment, the formulation comprises a cationic conditioning surfactant. In at least one embodiment, the formulation comprises from 0.05% to 3.0%, or from 0.075% to 2.0%, or from 0.1% to 1.0%, of cationic conditioning surfactant by total weight of the formulation. In at least one embodiment, the cationic conditioning surfactant is comprised in a lamellar gel matrix. In other words, the formulation comprises a lamellar gel matrix and the lamellar gel matrix comprises the cationic conditioning surfactant. In an embodiment, cationic conditioning surfactant is according to Formula (C):

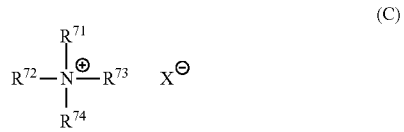

(C)

wherein at least one of $R^{71}$, $R^{72}$, $R^{73}$ and $R^{74}$ is selected from an aliphatic group of from 8 to 30 carbon atoms, an aromatic, alkoxy, polyoxyalkylene, alkylamido, hydroxyalkyl, aryl, or an alkylaryl group having up to 22 carbon atoms; the remainder of $R^{71}$, $R^{72}$, $R^{73}$ and $R^{74}$ are independently selected from the group consisting of an aliphatic group consisting of from 1 to 22 carbon atoms, and an aromatic, alkoxy, polyoxyalkylene, alkylamido, hydroxyalkyl, aryl or alkylaryl group having up to 22 carbon atoms;

X is selected from the group consisting of: halogen, acetate, citrate, lactate, glycolate, phosphate, nitrate, sulfonate, sulfate, alkylsulfate, alkyl sulfonate radicals, and combinations thereof.

In at least one embodiment, the cationic conditioning surfactant is selected from the group consisting of behenyl trimethyl ammonium chloride, methyl sulfate or ethyl sulfate, and stearyl trimethyl ammonium chloride, methyl sulfate or ethyl sulfate. It is believed that a longer alkyl group provides improved smoothness and soft feeling on wet and dry hair, compared to cationic surfactants with a shorter alkyl group. It is also believed that such cationic surfactants can provide reduced irritation, compared to those having a shorter alkyl group.

In at least one embodiment, the cationic surfactant is a di-long alkyl quatemized ammonium salt selected from the group consisting of: dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In at least one embodiment, the cationic surfactant is a tertiary amido amine having an alkyl group of from 12 to 22 carbons. The tertiary amido amine may be selected from the group consisting of stearamidopropyldimethyl-, stearamidopropyldiethyl-, stearamidoethyldiethyl-, stearamidoethyldimethyl-, palmitamidopropyldimethyl-, palmitamidopropyldiethyl-, palmitamidoethyldiethyl-, palmitamidoethyldimethyl-, behenamidopropyldimethyl-, behenamidopropyldiethyl-, behenamidoethyldiethyl-, behenamidoethyldimethyl-, arachidamidopropyldimethyl-, arachidamidopropyldiethyl-, arachidamidoethyldiethyl-, and arachidamidoethyldimethyl-amine, diethylaminoethylstearamide, and mixtures thereof. A tertiary amido amine may be used in combination with an acid. The acid is typically used as a salt-forming anion. In an embodiment, the acid is selected from the group consisting of lactic acid, malic acid, hydrochloric acid, 1-glumatic acid, acetic acid, citric acid, and mixtures thereof.

In at least one embodiment, the cationic surfactant is selected from the group consisting of cetyltrimonium chloride (CTAC), stearyltrimonium chloride (STAC), behentrimonium methosulfate, stearoylamidopropyldimethyl amine (SAPDMA), distearyldimethylammonium chloride, and mixtures thereof.

In at least one embodiment, the formulation comprises a surfactant system. In at least one embodiment, the surfactant system comprises a surfactant selected from the group consisting of anionic surfactants, cationic surfactants, nonionic surfactants, zwitterionic surfactants and/or amphoteric surfactants. In at least one embodiment, the formulation comprises a total amount of surfactant of from 0.01 wt.-% to 70 wt.-%, from 0.1 wt.-% to 40%, from 1 wt.-% to 30%, from 2 wt.-% to 20 wt.-%.

In at least one embodiment, the formulation comprises an anionic surfactant. In at least one embodiment, the anionic surfactant is selected from the group consisting of ($C_{10}$-$C_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, a-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, acylglutamates, and mixtures thereof. The anionic surfactants (and their mixtures) can be used in the form of their water-soluble or water-dispersible salts, examples being the sodium, potassium, magnesium, ammonium, mono, di-, and triethanolammonium, and analogous alkylammonium salts. In at least one embodiment, the anionic surfactant is the salt of an anionic surfactant comprising 12 to 14 carbon atoms. In at least one embodiment, the anionic surfactant is selected from the group consisting of sodium lauryl sulfate, sodium laureth sulfate, sodium tridecyl sulfate, sodium trideceth sulfate, sodium myristyl sulfate, sodium myreth sulfate, and mixtures thereof.

In at least one embodiment, the formulation comprises an acylglycinate surfactant. In at least one embodiment, the acylglycinate surfactant conforms to the formula (Y):

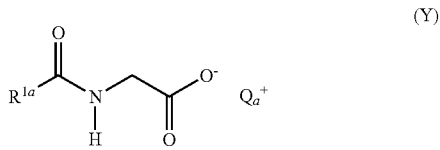

(Y)

wherein
$R^{1a}$ is a linear or branched, saturated alkanoyl group having 6 to 30, preferably 8 to 22, particularly preferably 8 to 18, carbon atoms or is a linear or branched, mono- or polyunsaturated alkenoyl group having 6 to 30, preferably 8 to 22, more preferably 12 to 18 carbon atoms, and $Q_a^+$ is a cation.

In at least one embodiment, $Q_a^+$ is selected from the group consisting of Li$^+$, Na$^+$, K$^+$, Mg$^{++}$, Ca$^{++}$, Al$^{+++}$, NH$_4^+$, a monoalkylammmoniumion, a dialkylammonium ion, a trialkylammonium ion and a tetraalkylammonium ion, or combinations thereof. Optionally R$^{1a}$ is independently from one another, are (C$_1$-C$_{22}$)-alkyl radicals or (C$_2$-C$_{10}$)-hydroxyalkyl radicals. In at least one embodiment, the acylglycinate surfactant is selected from sodium cocoylglycinate and potassium cocoylglycinate. In at least one embodiment, the acylglycinate surfactant is selected from those conforming to formula (Y), wherein R is C12 alkyl or C14 alkyl. In at least one embodiment, the acylglycinate surfactant is selected from those conforming to formula (Y), wherein R is C16 alkyl or C18 alkyl.

In at least one embodiment, the formulation comprises a glutamate surfactant corresponding to formula (Z) or a salt thereof:

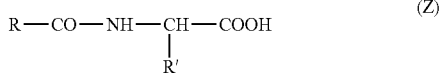

wherein
R' is HOOC—CH$_2$—CH$_2$— or M$^+$-OOC—CH$_2$—CH$_2$— wherein M$^+$ is a cation; and wherein R is a linear or branched, saturated alkanoyl group having 6 to 30, preferably 8 to 22, more preferably 8 to 18, carbon atoms or is a linear or branched, mono- or polyunsaturated alkenoyl group having 6 to 30, preferably 8 to 22 and more preferably 12 to 18 carbon atoms. In at least one embodiment, M$^+$ is a metal cation. In at least one embodiment, M$^+$ is selected from the group consisting of Li$^+$, Na$^+$, K$^+$, Mg$^{++}$, Ca$^{++}$, Al$^{+++}$, NH$_4^+$, a monoalkylammmonium ion, a dialkylammonium ion, a trialkylammonium ion and a tetraalkylammonium ion, or combinations thereof. In at least one embodiment, the glutamate surfactant is selected from sodium cocoyl glutamate and potassium cocoyl glutamate. In at least one embodiment, the glutamate surfactant is selected from those conforming to formula (Z), wherein R is C12 alkyl or C14 alkyl. In at least one embodiment, the glutamate surfactant is selected from those conforming to formula (Z), wherein R is C$_{16}$ alkyl or C$_{18}$ alkyl.

In at least one embodiment, the formulation comprises from 0.01 wt.-% to 30 wt.-%, or 1 wt.-% to 25 wt.-%, preferably from 5 wt.-% to 20 wt.-%, more preferably from 12 wt.-% to 18 wt.-% anionic surfactant.

In at least one embodiment, the formulation comprises a non-ionic surfactant. In at least one embodiment, the non-ionic surfactant has an HLB (Hydrophilic Lipophilic Balance) of greater than 12. Optionally, the non-ionic surfactant is selected from the group consisting of ethoxylated or ethoxylated/propoxylated fatty alcohols with a fatty chain comprising from 12 to 22 carbon atoms, ethoxylated sterols, such as stearyl- or lauryl alcohol (EO-7), PEG-16 soya sterol or PEG-10 soya sterol, polyoxyethylene polyoxypropylene block polymers (poloxamers), and mixtures thereof.

In at least one embodiment, the non-ionic surfactant is selected from the group consisting of ethoxylated fatty alcohols, fatty acids, fatty acid glycerides or alkylphenols, in particular addition products of from 2 to 30 mol of ethylene oxide and/or 1 to 5 mol of propylene oxide onto C$_8$- to C$_{22}$-fatty alcohols, onto C$_{12}$- to C$_{22}$-fatty acids or onto alkyl phenols having 8 to 15 carbon atoms in the alkyl group, C$_{12}$- to C$_{22}$-fatty acid mono- and diesters of addition products of from 1 to 30 mol of ethylene oxide onto glycerol, addition products of from 5 to 60 mol of ethylene oxide onto castor oil or onto hydrogenated castor oil, fatty acid sugar esters, in particular esters of sucrose and one or two C$_8$- to C$_{22}$-fatty acids, INCI:

Sucrose Cocoate, Sucrose Dilaurate, Sucrose Distearate, Sucrose Laurate, Sucrose Myristate, Sucrose Oleate, Sucrose Palmitate, Sucrose Ricinoleate, Sucrose Stearate, esters of sorbitan and one, two or three C$_8$- to C$_{22}$-fatty acids and a degree of ethoxylation of from 4 to 20, polyglyceryl fatty acid esters, in particular of one, two or more C$_8$- to C$_{22}$-fatty acids and polyglycerol having preferably 2 to 20 glyceryl units, alkyl glucosides, alkyl oligoglucosides and alkyl polyglucosides having C$_8$ to C$_{22}$-alkyl groups, e.g. decylglucoside or laurylglucoside, and mixtures thereof.

In at least one embodiment, the non-ionic surfactant is selected from the group consisting of fatty alcohol ethoxylates (alkylpolyethylene glycols), alkylphenol polyethylene glycols, alkylmercaptan polyethylene glycols, fatty amine ethoxylates (alkylaminopolyethylene glycols), fatty acid ethoxylates (acylpolyethylene glycols), polypropylene glycol ethoxylates)(Pluronics®, fatty acid alkylol amides, (fatty acid amide polyethylene glycols), N-alkyl-, N-alkoxypoly-hydroxy-fatty acid amide, sucrose esters, sorbitol esters, polyglycol ethers, and mixtures thereof.

In at least one embodiment, the formulation comprises a fatty N-methyl-N-glucamide surfactant, wherein the fatty N-methyl-N-glucamide surfactant conforms to the formula (X):

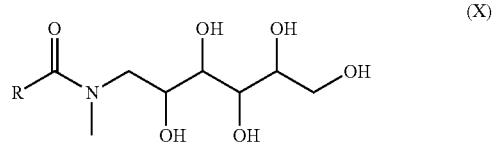

wherein R is a linear or branched alkyl or alkenyl group having from 3 to 30 carbon atoms. In at least one embodiment, R is an alkyl group having from 3 to 30 carbon atoms. In at least one embodiment, R is a saturated aliphatic hydrocarbon group which can be linear or branched and can have from 3 to 20 carbon atoms in the hydrocarbon chain, preferably linear or branched. Branched means that a lower alkyl group such as methyl, ethyl or propyl is present as substituent on a linear alkyl chain. In at least one embodiment, R is selected from the group consisting of 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl. Suitable fatty N-methyl-N-glucamide surfactants are described in WO-2013/178700 and EP-0550637, which are incorporated herein by reference. In at least one embodiment, the N-methyl-N-glucamide surfactant is selected from those conforming to formula (X), wherein R is C12 alkyl or C14 alkyl. In at least one embodiment, the N-methyl-N-glucamide surfactant is selected from those conforming to formula (X), wherein R is C16 alkyl or C18 alkyl.

In at least one embodiment, the formulation comprises from 1 wt.-% to 20 wt.-%, more preferably from 2 wt.-% to 10 wt.-%, even more preferably from 3 wt.-% to 7 wt.-% non-ionic surfactant.

In at least one embodiment, the amphoteric surfactants are selected from the group consisting of N—($C_{12}$-$C_{18}$)-alkyl-β-aminopropionates and N—(C12-C18)-alkyl-β-iminodipropionates as alkali metal salts and mono-, di-, and trialkylammonium salts; N-acylaminoalkyl-N,N-dimethylacetobetaine, preferably N—(C8-C18)-acylaminopropyl-N,N-dimethylacetobetaine, (C12-C18)-alkyl-dimethyl-sulfopropylbetaine, amphosurfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., (C12-C18)-alkyl-dimethyl-amine oxide, fatty acid amidoalkyldimethylamine oxide, and mixtures thereof.

In at least one embodiment, the formulation comprises a betaine surfactant. Optionally, the betaine surfactant is selected from $C_8$- to $C_{18}$-alkylbetaines. In at least one embodiment, the betaine surfactant is selected from the group consisting of cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and laurylbis(2-hydroxypropyl)alphacarboxyethylbetaine and combinations thereof. Optionally, the betaine surfactant is selected from $C_8$- to $C_{18}$-sulfobetaines. In at least one embodiment, the betaine surfactant is selected from the group consisting of cocodimethylsulfopropylbetaine, stearyldimethylsulfopropylbetaine, lauryldimethyl-sulfoethylbetaine, laurylbis(2-hydroxyethyl)sulfopropylbetaine, and combinations thereof. Optionally, the betaine surfactant is selected from carboxyl derivatives of imidazole, the $C_8$- to $C_{18}$-alkyldimethylammonium acetates, the $C_8$- to $C_{18}$-alkyldimethylcarbonylmethylammonium salts, and the $C_8$- to $C_{18}$-fatty acid alkylamidobetaines, and mixtures thereof. Optionally, the $C_8$- to $C_{18}$-fatty acid alkylamidobetaine is selected from coconut fatty acid amidopropylbetaine, N-coconut fatty acid amidoethyl-N-[2-(carboxymethoxy)ethyl] glycerol (CTFA name: Cocoamphocarboxyglycinate), and mixtures thereof.

In at least one embodiment, the formulation comprises from 0.5 wt.-% to 20 wt.-%, preferably from 1 wt.-% to 10 wt.-% amphoteric surfactant.

In at least one embodiment, the formulation comprises a surfactant system. In at least one embodiment, the surfactant system comprises at least one surfactant selected from the group consisting of lauryl sulfate, laureth sulfate, cocoamido-propylbetaine, sodium cocoylglutamate, lauroamphoacetate, and mixtures thereof. In at least one embodiment, the surfactant system comprises sodium laureth sulphate, sodium lauryl sulphate, and optionally cocamidopropyl betaine. In at least one embodiment, the surfactant system comprises sodium laureth sulphate, Potassium Cocyl Glutamate, and cocamidopropyl betaine.

In at least one embodiment, the formulation further comprises a hairstyling polymer. In at least one embodiment, the hairstyling polymer is selected from the group consisting of: amphoteric hairstyling polymers, zwitterionic hairstyling polymers, anionic hairstyling polymers, non-ionic hairstyling polymers, cationic hairstyling polymers, and mixtures thereof. In at least one embodiment, the formulation comprises from 0.01% to 20%, or from 0.01% to 16%, or from 0.01% to 10%, or from 1% to 8%, or from 2% to 6% of hairstyling polymer.

In at least one embodiment, the hairstyling polymer is a water-compatible hairstyling polymer, alternatively a water-soluble hairstyling polymer. In at least one embodiment, the formulation is substantially free of a water-incompatible hairstyling polymer. An example of a water-incompatible hairstyling polymer includes an Acrylates/t-Butylacrylamide Copolymer which is a copolymer of tert-butyl acrylamide and one or more monomers of acrylic acid, methacrylic acid, or one of their simple esters (e.g. Ultrahold® 8 from BASF). Balance® CR from Akzo Nobel, which is an acrylates copolymer of two or more monomers of (meth)acrylic acid or one of their simple esters, is water-compatible. The octylacrylamide/acrylate/butylaminoethyl methacrylate copolymer Amphomer® is also water-compatible. In at least one embodiment, the hairstyling polymer is a latex hairstyling polymer.

The formulation may comprise a cationic hairstyling polymer. In at least one embodiment, the cationic hairstyling polymers is selected from from group consisting of those with primary, secondary, tertiary or quaternary amino groups.

In at least one embodiment, the cationic hairstyling polymer has a cationic charge density, and wherein the cationic charge density is from 1 to 7 meq/g. In at least one embodiment, the cationic hairstyling polymer comprises quaternary amino groups. In at least one embodiment, the cationic hairstyling polymer is a homo- or copolymer where the quaternary nitrogen groups are contained either in the polymer chain or as substituents on one or more of the monomers. The ammonium group-containing monomers can be copolymerized with non-cationic monomers. In at least one embodiment, the cationic hairstyling polymer comprises cationic monomers where the cationic monomers are unsaturated compounds that can undergo radical polymerization and which bear at least one cationic group. In at least one embodiment, the cationic monomers are selected from the group consisting of: ammonium-substituted vinyl monomers such as, for example, trialkylmethacryloxyalkylammonium, trialkylacryloxyalkylammonium, dialkyldiallylammonium and quaternary vinylammonium monomers with cyclic, cationic nitrogen-containing groups such as pyridinium, imidazolium or quaternary pyrrolidones, e.g. alkylvinylimidazolium, alkylvinylpyridinium, or alkylvinylpyrrolidone salts. The alkyl groups of these monomers may be lower alkyl groups such, as for example, $C_1$- to $C_7$-alkyl groups, and may also be are $C_1$- to $C_3$-alkyl groups.

In at least one embodiment, cationic hairstyling polymer comprises ammonium group-containing monomers being copolymerized with non-cationic monomers. The non-cationic monomers may be selected from the group consisting of: acrylamide, methacrylamide, alkyl- and dialkylacrylamide, alkyl- and dialkylmethacrylamide, alkyl acrylate, alkyl methacrylate, vinylcaprolactone, vinylcaprolactam, vinylpyrrolidone, vinyl esters, for example vinyl acetate, vinyl alcohol, propylene glycol or ethylene glycol, and mixture thereof. The alkyl groups of these monomers may be $C_1$- to $C_7$-alkyl groups, and may be $C_1$- to $C_3$-alkyl groups. In at least one embodiment, cationic hairstyling polymer comprises at least one quaternary amino group. Suitable polymers with at least one quaternary amino group include, for example, those described in the CTFA Cosmetic Ingredient Dictionary under the designations 'polyquaternium' such as methylvinylimidazolium chloride/vinylpyrrolidone copolymer (polyquaternium-16) or quaternized vinylpyrrolidone/dimethylaminoethyl methacrylate copolymer (polyquaternium-11; Gafquat® 755N-PW from ISP) as well as quaternary silicone polymers or silicone oligomers such as, for example, silicone polymers with quaternary end groups (quaternium-80).

In at least one embodiment, the hairstyling polymer is a cationic hairstyling polymer being of synthetic origin. In at least one embodiment, the cationic hairstyling polymers of synthetic origin are selected from the group consisting of: poly(dimethyldiallylammonium chloride); copolymers from acrylamide and dimethyldiallylammonium chloride; quaternary ammonium polymers, formed by the reaction of diethyl sulfate with a copolymer from vinylpyrrolidone and dimethylaminoethyl methacrylate, especially vinylpyrrolidone/dimethylaminoethyl methacrylate methosulfate copolymer (e.g. Gafquat® 755 N; Gafquat® 734); quaternary ammonium polymers from methylvinylimidazolium chloride and vinylpyrrolidone (e.g. Luviquat® HM 550 from BASF; Luviquat® Hold from BASF; polyquaternium-46 [vinylcaprolactam {VCap}, vinylpyrrolidone {VP} and quaternized vinylimidazole {QVI}] from BASF; Luviquat® FC 905 from BASF [polyquaternium-16]); Luviquat Supreme® from BASF (polyquaternium-68, quaternised copolymer of vinyl pyrrolidone, methacrylamides, vinyl imidazole and quaternized vinyl imidazole); polyquaternium-35; polyquaternium-57; polymers from trimethylammonium ethyl methacrylate chloride; terpolymers from dimethyldiallylammonium chloride, sodium acrylate and acrylamide (e.g. Merquat® Plus 3300); copolymers from vinylpyrrolidone, dimethylaminopropyl methacrylamide, and methacryloylaminopropyllauryldimethylammonium chloride; terpolymers from vinylpyrrolidone, dimethylaminoethyl methacrylate, and vinylcaprolactam (e.g. Gaffix® VC 713); vinylpyrrolidone/methacrylamidopropyltrimethylammonium chloride copolymers (e.g. Gafquat® HS 100); copolymers from vinylpyrrolidone and dimethylaminoethyl methacrylate; copolymers from vinylpyrrolidone, vinylcaprolactam, and dimethylaminopropylacrylamide; poly- or oligoesters formed from at least one first type of monomer that is selected from hydroxyacids substituted with at least one quaternary ammonium group; dimethylpolysiloxane substituted with quaternary ammonium groups in the terminal positions; and mixtures thereof.

In at least one embodiment, the hairstyling polymer is a cationic hairstyling polymer being of natural origin. In at least one embodiment, the cationic hairstyling polymers being of natural origin are selected from the group consisting of: cationic derivatives of polysaccharides, for example, cationic cellulose derivatives, starch, guar, and mixtures thereof. Cationic derivatives of polysaccharides may be represented by the general formula:

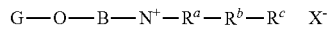

wherein

| | |
|---|---|
| G | is an anhydroglucose residue, for example, starch or cellulose anhydroglucoses; |
| B | is a divalent bonding group, for example, alkylene, oxyalkylene, polyoxyalkylene or hydroxyalkylene; |
| $R^a$, $R^b$ and $R^c$ | are, independently from one another, alkyl, aryl, alkylaryl, arylalkyl, alkoxyalkyl or alkoxyaryl, any of which can have up to 22 carbon atoms, wherein the total number of carbon atoms in $R^a$, $R^b$ and $R^c$ is may be a maximum of 20. |

In at least one embodiment, the hairstyling polymer is a cationic cellulose derivative being selected from the group consisting of: those that have at least one quaternary ammonium group, e.g. a copolymer made of hydroxyethyl cellulose and diallyldimethyl ammonium chloride (polyquaternium-4), or the reaction product made of hydroxyethyl cellulose and an epoxide substituted with a trialkyl ammonium group (polyquaternium-10), wherein the alkyl groups can have 1 to 20 carbon atoms, or wherein the alkyl group is methyl. In at least one embodiment, the hairstyling polymer is a cationic cellulose derivative having a molecular weight of from 100,000 Da to 600,000 Da, or from 200,000 Da to 400,000 Da. In at least one embodiment, the cationic cellulose derivative has a nitrogen content, wherein the nitrogen content is from 0.5% to 4%, or from aout 1.5% to 3%. In at least one embodiment, the hairstyling polymer is a cationic cellulose derivative being polyquaternium-4. Polyquaternium-4 is sold under the trade names Celquat® H1OO and Celquat® L200, of which Celquat® L200 is especially preferred.

In at least one embodiment, the hairstyling polymer is a cationic latex hairstyling polymer. In at least one embodiment, the cationic hairstyling polymer is selected from the group consisting of: polyquaternium-4, polyquaternium-11, polyquaternium-16, polyquaternium-68, mixtures thereof, and mixtures of polyquaternium-68 with a non-ionic hairstyling polymer. In at least one embodiment, the hairstyling polymer is selected from the group consisting of: polyquaternium-4, polyquaternium-11, polyquaternium-68, and mixtures thereof. In at least one embodiment, the formulation comprises a chitosan, a chitosan salt or a chitosan derivative. In at least one embodiment, the formulation comprises less than 0.1% by weight chitosan, chitosan salts and chitosan derivatives. In another embodiment, the formulation is substantially free from chitosan, chitosan salts and chitosan derivatives. In at least one embodiment, the formulation comprises a hairstyling polymer selected from the group consisting of: polyquaternium-4, polyquaternium-11, polyquaternium-16, polyquaternium-68, mixtures thereof; or from the group consisting of: polyquaternium-4, polyquaternium-68, and mixtures thereof. In at least one embodiment, the formulation comprises a hairstyling polymer selected from the group consisting of: polyquaternium-4, polyquaternium-11, polyquaternium-68, mixtures thereof; or from the group consisting of: polyquaternium-4, polyquaternium-68, and mixtures thereof.

In at least one embodiment, the formulation comprises less than 0.5 wt.-% of a cationic hairstyling polymer by total weight of the formulation.

In at least one embodiment, the formulation comprises an amphoteric or zwitterionic hairstyling polymer. In at least one embodiment, the amphoteric or zwitterionic hairstyling polymer is selected from the group consisting of: copolymers formed from alkylacrylamide, alkylaminoalkyl methacrylate, and two or more monomers from acrylic acid and methacrylic acid as well as, if necessary, their esters, especially copolymers from octylacrylamide, acrylic acid, butylaminoethyl methacrylate, methyl methacrylate and hydroxypropyl methacrylate (octylacrylamide/acrylate/butylaminoethyl methacrylate copolymer, for example Amphomer® from Akzo Nobel); copolymers, that are formed from at least one of a first type of monomer that possesses quaternary amino groups and at least one of a second type of monomer that possesses acid groups; copolymers from fatty alcohol acrylates, alkylamine oxide methacrylate and at least one monomer selected from acrylic acid and methacrylic acid as well as, if necessary, acrylic acid esters and methacrylic acid esters, especially copolymers from lauryl acrylate, stearyl acrylate, ethylamine oxide methacrylate and at least one monomer selected from acrylic acid and methacrylic acid as well as, if necessary, their esters; copolymers from methacryloyl ethyl betaine and at least one monomer selected from methacrylic acid and methacrylic acid esters; copolymers from acrylic acid, methyl acrylate and methacrylamidopropyltrimethylammonium chloride (polyquaternium-47); copolymers from acrylamidopropyltrimethylammonium chloride and acrylates or copolymers from acrylamide, acrylamidopropyltrimethylammonium chloride, 2-amidopropylacrylam ide sulfonate and dimethylaminopropylamine (polyquaternium-43); oligomers or polymers, producible from quaternary crotonoylbetaines or quaternary crotonoylbetaine esters. In at least one embodiment, the formulation comprises an amphoteric or zwitterionic latex hairstyling polymer. In at least one embodiment, the hairstyling polymer is selected from the group consisting of: polyquaternium-47, octylacrylamide/acrylate/butylaminoethyl methacrylate copolymers, and mixtures thereof.

The hairstyling formulation may comprise an anionic hairstyling polymer. In at least one embodiment, the anionic hairstyling polymer is selected from the group consisting of: acrylates copolymers of two or more monomers of (meth) acrylic acid or one of their simple esters (e.g. Balance® CR from Akzo Nobel); acrylates/hydroxyesters acrylates copolymers including those being copolymers of butyl acrylate, methyl methacrylate, methacrylic acid, ethyl acrylate and hydroxyethyl methacrylate (e.g. Acudyne™ 1000 from Dow Personal Care); terpolymers of acrylic acid, ethyl acrylate, and N-tert-butylacrylamide; crosslinked or uncrosslinked vinyl acetate/crotonic acid copolymers; terpolymers of tert-butylacrylate, ethyl acrylate and methacrylic acid; sodium polystyrenesulfonate; copolymers of vinyl acetate, crotonic acid and vinyl propionate; copolymers of vinyl acetate, crotonic acid and vinyl neodecanoate; aminomethylpropanol/acrylate copolymers; copolymers of vinylpyrrolidone and at least one further monomer selected from among acrylic acid, methacrylic acid, acrylic acid esters and methacrylic acid esters; copolymers of methyl vinyl ether and maleic acid monoalkyl esters; aminomethylpropanol salts of copolymers of allyl methacrylate and at least one further monomer selected from among acrylic acid, methacrylic acid, acrylic acid esters and methacrylic acid esters; crosslinked copolymers of ethyl acrylate and methacrylic acid; copolymers of vinyl acetate, mono-n-butyl maleate and isobornyl acrylate; copolymers of two or more monomers selected from among acrylic acid, methacrylic acid, acrylic acid esters and methacrylic acid esters, copolymers of octylacrylamide and at least one monomer selected from among acrylic acid, methacrylic acid, acrylic acid esters and methacrylic acid esters; polyesters of diglycol, cyclohexanedimethanol, isophthalic acid and sulfoisophthalic acid; polyurethanes; and copolymers of polyurethane and acrylates. e.g. polyurethane-14/AMP-acrylates polymer blend (e.g. DynamX® from Akzo Nobel). Suitable polyester polymers include polyester-5 polymers, for example AQ® 48 Ultra Polymer, (diglycol/CHDM/isophthalates/SIP copolymer [a copolymer of diethylene glycol, 1,4-cyclohexanedimethanol and the simple esters of isophthalic acid and sulfoisophthalic acid]), AQ® 55 S, and AQ® 38 S, all from Eastman Chemical Company. Also suitable is a polyvinylmethacrylic acid/maleic acid copolymer (Omnirez® 2000 from ISP). Anionic latex hairstyling polymers are also suitable. In at least one embodiment, the anionic hairstyling polymer is selected from the group consisting of: polyurethane-1 (e.g. Luviset® P.U.R. from BASF), polyurethane-14/AMP-acrylates copolymer blend (e.g. DynamX® from Akzo Nobel), acrylates copolymers of two or more monomers of (meth) acrylic acid or one of their simple esters (e.g. Balance® CR from Akzo Nobel), and mixtures thereof. In at least one embodiment, the anionic hairstyling polymer is Polyurethane-1.

The formulation may comprise a non-ionic hairstyling polymer. In at least one embodiment, the formulation comprises a non-ionic hairstyling polymer, wherein are non-ionic hairstyling polymer is a homo- or copolymer that is formed from at least one of the following monomers: vinylpyrrolidone, vinylcaprolactam, vinyl esters such as, for example, vinyl acetate, vinyl alcohol, acrylamide, methacrylamide, alkyl- and dialkylacrylamide, alkyl- and dialkylmethacrylamide, alkyl acrylate, alkyl methacrylate, propylene glycol or ethylene glycol, where the alkyl groups in these monomers may be $C_1$- to $C_7$-alkyl groups or $C_1$- to C3-alkyl groups. In at least one embodiment, the formulation comprises a homopolymer selected from the group consisting of: vinylcaprolactam, vinylpyrrolidone, N-vinylformamide and mixtures thereof. In at least one embodiment, the non-ionic hairstyling polymer is selected from the group consisting of: copolymers of vinylpyrrolidone and vinyl acetate, terpolymers of vinylpyrrolidone, vinyl acetate and vinyl propionate, polyacrylam ides; polyvinyl alcohols as well as polyethylene glycol/polypropylene glycol copolymers; and mixtures thereof. In at least one embodiment, the non-ionic hairstyling polymer is selected from the group consisting of: polyvinylpyrrolidone/dimethylaminopropylaminoacrylates copolymer (Aquaflex® SF 40 from ISP); isobutylene ethylmaleinimide/hydroxy ethylmaleinimide copolymer (Aquaflex® FX 64 from ISP); vinylcaprolactam/polyvinylpyrrolidone/dimethylaminoethyl methacrylate copolymer (Advantage® from ISP); and mixtures thereof. Non-ionic latex hairstyling polymers are also suitable. In at least one embodiment, the non-ionic hairstyling polymer is selected from the group consisting of: polyvinylpyrrolidone (K90, 85, 80, 60, 30), polyvinylpyrrolidone/vinyl acetate copolymers (PVP/VA 64), terpolymers of vinylpyrrolidone, methacrylamide and vinylimidazole (e.g. Luviset® Clear from BASF), and mixtures thereof. In at least one embodiment, the non-ionic hairstyling polymer is selected from the group consisting of: PVP K 60, 30, and PVP/VA 37/64. In at least one embodiment, the non-ionic hairstyling polymer is selected from the group consisting of: PVP K60 and PVP/VA 37/64.

In at least one embodiment, the formulation comprises an anionic latex hairstyling polymer. In at least one embodiment, the anionic latex hairstyling polymer is a urethane-based polymer, for example polyurethane-34 (Baycusan® from Bayer). Polyurethane-34 is described in EP-2105127A1. In at least one embodiment, the hairstyling polymer is the latex hairstyling polymer polyurethane-34.

In at least one embodiment, the anionic hairstyling polymer and/or cationic hairstyling polymer is present in neutralized or partially neutralized form. In at least one embodiment, the formulation comprises a neutralising agent, and wherein the neutralising agent is selected from the group consisting of: potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia (NH3), triethanolamine, trimethylamine (Tris Amino Ultra), aminomethylpropandiol (AMPD) and mixtures thereof. In at least one embodiment, the neutralising agent is 2-aminomethyl propanol.

In at least one embodiment, the formulation has a viscosity of from 0 cPs to 20,000 cPs. In at least one embodiment, the formulation has a viscosity of from 0.1 cPs to 10,000 cPs, or from 1 cPs to 5,000 cPs, or from 5 cPs to 3,500 cPs. The viscosity measurement conditions are defined in the definitions section above. Viscosity may be important for anti-drip reasons. Dripping can be inconvenient for the user. Furthermore, more viscous formulations can be useful for measured dispensing. In at least one embodiment, the formulation has a viscosity of from 0 cPs to 1,000 cPs. This viscosity range is advantageous when the formulation is in the form of a facial cleanser in view of the need for distribution on skin and ability to rinse off.

In at least one embodiment, the formulation further comprises a viscosity-modifying substance. The viscosity-modifying substance is preferably a thickening polymer.

In at least one embodiment, the thickening polymer is a polymers based on acrylamidomethylpropanesulfonic acid (AMPS®, Lubrizol). These polymers, even at pH values of 7 or less, exhibit good thickening performance. Especially preferably, the thickening polymer is selected from the group consisting of homo- or copolymers of acrylamidomethylpropanesulfonic acid and salts thereof. Among the polymers just mentioned, preference is in turn given to polymers having at least 20 mol-% of units based on acrylamidomethylpropanesulfonic acid and/or salts thereof, and particular preference to polymers having at least 50 mol-% of units based on acrylamidomethylpropanesulfonic acid and/or salts thereof, the mole figures relating in each case to the overall polymer. In the case of the copolymers, as well as structural units based on acrylamidomethylpropanesulfonic acid and/or salts thereof, preferably one or more structural units based on the following comonomers are present in the copolymers: acrylic acid, methacrylic acid, acrylamide, dimethylacrylamide, vinylpyrrolidone (VP), hydroxyethyl acrylate, hydroxyethyl methacrylate, acrylic or methacrylic esters of ethoxylated alcohols RO—$(CH_2CH_2O)_m$H, in which R is an alkyl radical having 12 to 30 carbon atoms and m is a number from 3 to 30, and $CH_2$=CH—COO—$(CH_2CH_2$—COO$)_n$X in which n is a number from 0 to 10 and X is a counterion and is preferably $H^+$, $Na^+$ and/or $NH_4^+$. The polymers selected from the group consisting of homo- or copolymers of acrylamidomethylpropanesulfonic acid and salts thereof may be crosslinked or uncrosslinked. In the case of crosslinking, they contain structural units based on monomers having 2 or more olefinic double bonds. In the case of crosslinking, preferably from 0.1 to 10 mol-% of such structural units are present in the homo- or copolymers, based on the overall polymer. If one or more structural units based on acrylamidomethylpropanesulfonic acid and/or salts thereof in the homo- or copolymers of acrylamidomethylpropanesulfonic acid and/or salts thereof have one or more counterions other than $H^+$, these other counterions are preferably selected from the group consisting of $Na^+$ and $NH_4^+$. Suitable polymers are mentioned in publications including EP-0816403, EP-1069142, EP-1116733 and DE-10 2009 014877 (Clariant), EP-1347736 (L'Oreal) or EP-1496081 (Seppic). Examples include: Aristoflex® AVC (Ammonium Acryloyldimethyltaurate/VP Copolymer), Aristoflex® AVS (Sodium Acryloyldimethyltaurate/VP Crosspolymer), Aristoflex® TAC (Ammonium Acryloyl Dimethyltaurate Carboxyethyl Acrylate Crosspolymer), Hostacerin® AMP5 (Ammonium Polyacryloyldimethyl Taurate), Aristoflex® HMB (Ammonium Acryloyldimethyltaurate/Beheneth-25 Methacrylate Crosspolymer), Aristoflex® BLV (Ammonium Acryloyldimethyltaurate/Beheneth-25 Methacrylate Crosspolymer), Aristoflex® HMS (Ammonium Acryloyldimethyl-taurate/Steareth-25 Methacrylate Crosspolymer), Aristoflex® SNC (Ammonium Acryloyldimethyltaurate/Steareth-8 Methacrylate Copolymer), Aristoflex® LNC (Ammonium Acryloyldimethyltaurate/Laureth-7 Methacrylate Copolymer) or Sepinov® EMT 10 (Hydroxyethyl Acrylate/Sodium Acryloyldimethyl Taurate Copolymer), Sepigel® 305.

In at least one embodiment, the thickening polymer selected from the group consisting of: copolymers of at least one first monomer type, which is chosen from acrylic acid and methacrylic acid, and at least one second monomer type, which is chosen from esters of acrylic acid and ethoxylated fatty alcohol; crosslinked polyacrylic acid; crosslinked copolymers of at least one first monomer type, which is chosen from acrylic acid and methacrylic acid, and at least one second monomer type, which is chosen from esters of acrylic acid with $C_{10}$- to $C_{30}$-alcohols; copolymers of at least one first monomer type, which is chosen from acrylic acid and methacrylic acid, and at least one second monomer type, which is chosen from esters of itaconic acid and ethoxylated fatty alcohol; copolymers of at least one first monomer type, which is chosen from acrylic acid and methacrylic acid, at least one second monomer type, which is chosen from esters of itaconic acid and ethoxylated $C_{10}$- to $C_{30}$-alcohol and a third monomer type, chosen from $C_1$- to $C_4$-aminoalkyl acrylates; copolymers of two or more monomers chosen from acrylic acid, methacrylic acid, acrylic esters and methacrylic esters; copolymers of vinylpyrrolidone and ammonium acryloyldimethyltaurate; copolymers of ammonium acryloyldimethyltaurate and monomers chosen from esters of methacrylic acid and ethoxylated fatty alcohols; hydroxyethylcellulose; hydroxypropylcellulose; hydroxypropylguar; glyceryl polyacrylate; glyceryl polymethacrylate; copolymers of at least one $C_2$-, $C_3$- or $C_4$-alkylene and styrene; polyurethanes; hydroxypropyl starch phosphate; polyacrylamide; copolymer of maleic anhydride and methyl vinyl ether crosslinked with decadiene; carob seed flour; guar gum; xanthan; dehydroxanthan; carrageenan; karaya gum; hydrolyzed corn starch; copolymers of polyethylene oxide, fatty alcohols and saturated methylenediphenyl diisocyanate (e.g. PEG-150/stearyl alcohol/SMDI copolymer); and mixtures thereof.

In at least one embodiment, the formulation has a pH value of from 2.0 to 12.0, preferably from 3.0 to 9.0, more preferably from 4.5 to 7.5. By varying the pH value, a formulation can be made available that is suitable for different applications.

In at least one embodiment, the formulation comprises an alkalizing agent or pH adjusting agent. In at least one embodiment, ammonia or caustic soda is suitable, but water-soluble, physiologically tolerable salts of organic and inorganic bases can also be considered. Optionally, the pH adjusting agent is selected from ammonium hydrogen carbonate, ammonia, monoethanolamine, ammonium carbonate. In at least one embodiment, the alkalizing agents is selected from the group consisting of 2-amino-2-methyl-1-propanol, 2-amino-2-methyl-1,3-propanediol, 2-amino-2-ethyl-1,3-propanediol, tris(hydroxyl-methyl)-aminomethane, 2-amino-1-butanole, tris-(2-hydroxypropyl)-amine, 2,2-iminobisethanol, lysine, iminourea (guanidine carbonate), tetrahydro-1,4-oxazine, 2-amino-5-guanidin-valeric acid, 2-aminoethansulfonic acid, diethanolamine, triethanolamine, N-methyl ethanolamine, isopropanolamine, diisopropanolamine, triisopropanolamine, glucamine, sodium hydroxide, potassium hydroxide, lithium hydroxide and magnesium oxide, and mixtures thereof.

To establish an acidic pH value, and acid can be included. In at least one embodiment, the formulation comprises an acid selected from the group consisting of hydrochloric acid, phosphoric acid, acetic acid, formic acid, sulfuric acid, hydrochloric acid, citric acid, and mixtures thereof. Citric acid is most preferred in that it has high consumer acceptance. In at least one embodiment, the acidic pH is adjusted with a buffer such as a phosphate buffer, a TRIS buffer or a citric buffer. The buffers may be used alone or in combination with an acid.

In at least one embodiment, the formulation is in liquid form. In an alternative embodiment, the formulation is in solid form. Optionally, the formulation is in powdered or granulated form. This is advantageous in that it is not needed to ship liquid, which are typically heavy over long distances, which has economic and environmental benefits. A solid form can be achieved by spray drying the formulation or the employment of a rotary evaporator. The formulation can be converted into liquid form after it has been shipped e.g. by adding water.

In at least one embodiment, the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

In at least one embodiment, the formulation is a household cleansing formulation.

In at least one embodiment, the formulation is a hand dishwashing formulation. In at least one embodiment, the hand dishwashing formulation comprises an anionic surfactant. In at least one embodiment, the hand dishwashing formulation comprises from 5 wt.-% to 25 wt.-% anionic surfactant. In at least one embodiment, the hand dishwashing formulation comprises a surfactant system comprising at least one anionic surfactant and a further surfactant selected from non-ionic surfactants, amphoteric surfactants, or zwitterionic surfactants. Preferably, the hand dishwashing formulation comprises cocoamidopropylbetaine or an amine oxide. Preferably the amine oxide is lauryl amine oxide, cocoyl amine oxide, or a combination thereof. In at least one embodiment, the pH value of the hand dishwashing formulation is between pH 5.0 and pH 10, preferably pH 5,5 to 9.0. In the case of the hand dishwashing formulation comprising an amine oxide, the hand dishwashing formulation preferably has a pH of between pH 7.5 and pH 9.5, most preferably pH 8.0 and pH 9.0.

In at least one embodiment, the formulation is a hard surface cleaner. In at least one embodiment, the hard surface cleaner comprises an anionic surfactant. In at least one embodiment, the hard surface cleaner comprises from 1 wt.-% to 10 wt.-% anionic surfactant. In at least one embodiment, the hard surface cleaner comprises a nonionic surfactant. In at least one embodiment, the hard surface cleaner comprises from 1 wt.-% to 10 wt.-% nonionic surfactant. In at least one embodiment, the hard surface cleaner comprises a surfactant system comprising at least one anionic surfactant and a further surfactant selected from non-ionic surfactants, amphoteric surfactants, and zwitterionic surfactants, or combinations thereof. Preferably, the hard surface cleaner comprises linear alkylbenzenesulfonate and fatty alcohol ethoxylate. In at least one embodiment, the pH value of the hard surface cleaner is between pH 5.0 and pH 11, preferably from pH 6.0 to pH 9.0.

In at least one embodiment, the formulation is a liquid laundry detergent formulation comprising one or more surfactants. Preferably, the one or more surfactants of the liquid laundry detergent formulation are selected from the group consisting of anionic, nonionic, cationic and zwitterionic surfactants, and more preferably from the group consisting of anionic, nonionic and zwitterionic surfactants.

Anionic Surfactants

In at least one embodiment, the formulation comprises an anionic surfactant. Anionic surfactants are particularly useful in cleansing formulations such as household cleansing formulations. Preferred anionic surfactants are alkyl sulfonates and alkyl ether sulfates.

Preferred alkyl sulfonates are alkylbenzene sulfonates, particularly linear alkylbenzene sulfonates (LAS) having an alkyl chain length of C8-C15. Possible counterions for concentrated alkaline liquids are ammonium ions, e.g. those generated by the neutralization of alkylbenzene sulfonic acid with one or more ethanolamines, for example monoethanolamine (MEA) and triethanolamine (TEA), or alternatively, alkali metals, e.g. those arising from the neutralization of alkylbenzene sulfonic acid with alkali hydroxides. The linear alkyl benzene sulfonate surfactants may be LAS with an alkyl chain length of preferably from 8 to 15 and more preferably from 12 to 14. Preferred alkyl ether sulfates (AES) are alkyl polyethoxylate sulfate anionic surfactants.

Nonionic Surfactants

In at least one embodiment, the formulation comprises a nonionic surfactant. Nonionic surfactants include primary and secondary alcohol ethoxylates, especially C8-C20 aliphatic alcohol ethoxylated with an average of from 1 to 20 moles of ethylene oxide per mole of alcohol, and more especially the C10-C15 primary and secondary aliphatic alcohols ethoxylated with an average of from 1 to 10 moles of ethylene oxide per mole of alcohol. Non-ethoxylated nonionic surfactants include alkyl polyglycosides, glycerol monoethers and polyhydroxy amides (glucamide). Mixtures of nonionic surfactants may be used.

When included therein, the household cleansing formulation, particularly the liquid laundry detergent formulation, preferably comprises from 0.2 wt.-% to 40 wt. %, more preferably 1 wt.-% to 20 wt.-% nonionic surfactant, such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, N-acyl N-alkyl derivatives of glucosamine ("glucamides"), or combinations thereof. The nonionic surfactants that may be used include the primary and secondary alcohol ethoxylates, especially the C8-C20 aliphatic alcohols ethoxylated with an average of from 1 to 35 moles of ethylene oxide per mole of alcohol, and more especially the C10-C15 primary and secondary aliphatic alcohols ethoxylated with an average of from 1 to 10 moles of ethylene oxide per mole of alcohol.

Zwitterionic Surfactants

In at least one embodiment, the formulation comprises a zwitterionic surfactant. The liquid laundry detergent formulation may comprise a zwitterionic surfactant, e.g. amine oxide or betaine, preferably in an amount of up to 10 wt.-% based on the total weight of the liquid laundry detergent formulation.

Betaines may be alkyldimethyl betaines or alkylamido betaines, wherein the alkyl groups have C12-18 chains.

Additional Surfactants

In at least one embodiment, the liquid laundry detergent formulation comprises a surfactant selected from the group consisting of anionic surfactants, nonionic surfactants, and mixtures thereof; preferably the surfactant is selected from the group consisting of linear alkyl benzene sulfonates, alkyl ether sulfates, nonionic surfactants, amine oxides and betaines; and more preferably selected from the group consisting of linear alkyl benzene sulfonates, alkyl ether sulfates and nonionic surfactants.

Other surfactants than the preferred LAS, AES, and nonionic surfactants may be added to the formulation according to the sixth aspect.

Although less preferred, some alkyl sulfate surfactant may be used, especially the non-ethoxylated C12-15 primary and secondary alkyl sulfates. Soap may also be used. Levels of soap are preferably lower than 10 wt.-%.

Preferably, the one or more surfactants in the liquid laundry detergent formulations, are present in an amount of at least 5 wt.-%, more preferably from 5 wt.-% to 65 wt.-%, even more preferably from 6 to 60 wt.-% and extraordinarily preferably from 7 wt.-% to 55 wt.-%, in each case based on the total weight of the liquid laundry detergent formulation.

Further Optional Ingredients

The household cleansing formulations may comprise one or more optional ingredients, e.g. they may comprise conventional ingredients commonly used in detergent compositions, especially laundry detergent compositions. Examples of optional ingredients include, but are not limited to builders, bleaching agents, bleach active compounds, bleach activators, bleach catalysts, photobleaches, dye transfer inhibitors, colour protection agents, anti-redeposition agents, dispersing agents, fabric softening and antistatic agents, fluorescent whitening agents, enzymes, enzyme stabilizing agents, foam regulators, defoamers, malodour reducers, preservatives, disinfecting agents, hydrotropes, fibre lubricants, anti-shrinkage agents, buffers, fragrances, processing aids, colorants, dyes, pigments, anti-corrosion agents, fillers, stabilizers and other conventional ingredients for washing or laundry detergent compositions.

Polymer

For detergency boosting, it may be advantageous to use a polymer in the household cleansing formulations, particularly in the liquid laundry detergent formulations. This polymer is preferably a polyalkoxylated polyethyleneimine (EPEI). Polyethylene imines are materials composed of ethylene imine units —$CH_2CH_2NH$— and, where branched, the hydrogen on the nitrogen is replaced by another chain of ethylene imine units. These polyethyleneimines can be prepared, for example, by polymerizing ethyleneimine in the presence of a catalyst such as carbon dioxide, sodium bisulfite, sulfuric acid, hydrogen peroxide, hydrochloric acid, acetic acid, and the like. Specific methods for preparing these polyamine backbones are disclosed in U.S. Pat. Nos. 2,182,306, 3,033,746, 2,208,095, 2,806,839, and 2,553,696.

The household cleansing formulations, particularly the liquid laundry detergent formulations, may comprise other polymeric materials, for example: dye transfer inhibition polymers, anti-redeposition polymers and cotton soil release polymers, especially those based on modified cellulosic materials. Especially, when EPEI is not present, the formulation may further comprise a polymer of polyethylene glycol and vinyl acetate, for example the lightly grafted copolymers described in WO 2007/138054. Such amphiphilic graft polymers based on water soluble polyalkylene oxides as graft base and side chains formed by polymerisation of a vinyl ester component have the ability to enable reduction of surfactant levels whilst maintaining high levels of oily soil removal.

Hydrotropes

In at least one embodiment, the formulation comprises a hydrotrope. Herein "hydrotrope" is a solvent that is neither water nor conventional surfactant, and that aids the solubilisation of surfactants and other components, especially any polymer and/or sequestrant, in the liquid, to render it isotropic. Hydrotropes are particularly useful in household cleansing formulations. Among suitable hydrotropes the following are noteworthy: monopropylene glycol (MPG), glycerol, sodium cumene sulfonate, ethanol, other glycols, e.g. dipropylene glycol, diethers and urea. MPG and glycerol are preferred hydrotropes.

Enzymes

In at least one embodiment, the formulation, particularly the liquid laundry detergent formulation, comprises an enzyme. In at least one embodiment, the enzyme is selected from the group consisting of protease, mannanase, pectate lyase, cutinase, esterase, lipase, amylase, cellulase, and combinations thereof. Less preferred additional enzymes may be selected from peroxidase and oxidase. The enzymes are preferably present with corresponding enzyme stabilizers. The total enzyme content in the formulation is preferably from 0 wt. % to 5 wt.-%, more preferably from 0.5 wt.-% to 5 wt.-% and even more preferably from 1 wt.-% to 4 wt.-%, by total weight of the formulation.

Sequestrants

Sequestrants are preferably included in the formulation, particularly in the household cleansing formulations. Preferred sequestrants include organic phosphonates, alkanehydroxy phosphonates and carboxylates available under the DEQUEST trade mark from Thermphos. The preferred sequestrant level is less than 10 wt.-% and preferably less than 5 wt.-% by total weight of the formulation. A particularly preferred sequestrant is HEDP (1-hydroxyethylidene-1,1-diphosphonic acid), for example sold as Dequest 2010. Also suitable but less preferred as it gives inferior cleaning results is Dequest® 2066 (diethylenetriamine penta(methylene-phosphonic acid) or Heptasodium DTPMP).

Buffers

In at least one embodiment, the formulation, particularly the liquid laundry detergent formulation, comprises a buffer. In addition to agents optionally included for the generation of anionic surfactants, e.g. from LAS or fatty acids, the presence of buffer is preferred for pH control. Possible buffers are one or more ethanolamines, e.g. monoethanolamine (MEA) or triethanolamine (TEA). They are preferably used in formulation at levels of from 1.0 to 15 wt.-%.

Other suitable amino alcohol buffer materials may be selected from the group consisting of compounds having a molecular weight above 61 g/mol, which includes MEA. Suitable materials also include, in addition to the already mentioned materials: monoisopropanolamine, diisopropanolamine, triisopropanolamine, monoamino hexanol, 2-[(2-methoxyethyl) methylamino]-ethanol, propanolamine, N methylethanolamine, diethanolamine, monobutanolamine, isobutanolamine, monopentanolamine, 1-amino-3-(2-methoxyethoxy)-2-propanol, 2-methyl-4-(methylamino)-2-butanol and mixtures thereof.

Potential alternatives to amino ethanol buffers are alkali hydroxides such as sodium hydroxide or potassium hydroxide.

EXAMPLES

The examples which follow are intended to illustrate the subject matter of the invention without restricting it thereto.

Synthesis Examples of the Compound X of the First Aspect

Synthesis Example 1: Preparation of N-Octanoyl-N-Methyl Cyclic Glucamide

In a 250 mL glass flask (equipped with stirrer, dropping funnel, water separator, nitrogen line and vacuum line) 221.8 g of a ca. 44% aqueous solution of N-Methyl-Glucamine (0.50 mol) are placed. While stirring, this solution is heated up to 135° C. to evaporate water. Then 30 mbar vacuum is applied for 1 h at 135° C. Afterwards temperature is increased to 160° C. and vacuum is broken with nitrogen. 72.1 g (0.50 mol) of tempered octanoic acid (120° C.) is added slowly to the hot melt of N-Methyl-Glucamine to avoid foaming and gel phases. With a moderate stream of nitrogen the reaction mixture is stirred for additional hours (about 6) to get the acid concentration below 1% (titration of acid number) and reaction water is collected over the whole time. Then the hot mixture is filled in a suitable glass bottle. You get 150 g of a yellow to brownish high viscous liquid.

The resultant product contains 92% of the desired N-Octanoyl-N-Methyl cyclic Glucamide measured by GC after derivatisation.

Synthesis Example 2

The steps as per synthesis example 1 are followed except that the (0.50 mol) of tempered octanoic acid (120° C.) is replaced with 0.50 mol of tempered decanoic acid (120° C.). The resultant product contains N-Decanoyl-N-Methyl cyclic Glucamide measured by GC after derivatisation.

Synthesis Example 3

The steps as per synthesis example 1 are followed except that the (0.50 mol) of tempered octanoic acid (120° C.) is replaced with 0.50 mol of a mixture of tempered (120° C.) decanoic acid and octanoic acid. The resultant product contains a mixture of N-Octanoyl-N-Methyl cyclic Glucamide and N-Decanoyl-N-Methyl cyclic Glucamide measured by GC after derivatisation.

TABLE 1

Example compositions of the first aspect

| | Example | | | | | | | | |
|---|---|---|---|---|---|---|---|---|---|
| | 1 | 2 | 3 | 4 | 5 | 6 | 7 | 8 | 9 |
| * N-decanoyl-N-methyl cyclic glucamide | — | 92 | 15 | — | 30 | 35 | 85 | 40 | — |
| # N-octanoyl-N-methyl cyclic glucamide | 60 | — | 15 | 92 | 30 | 47 | — | 40 | 30 |
| A compound according to Formula (2) and/or (3) | — | — | — | — | — | 8 | — | 1 | 5 |
| Other by-products | — | 8 | — | 8 | — | 10 | 5 | 4 | 2 |
| Water | 40 | — | 70 | — | 40 | — | 10 | 15 | 63 |
| Total [%] | 100 | 100 | 100 | 100 | 100 | 100 | 100 | 100 | 100 |

KEY:
* = compound according to Formula (I), wherein R is —(CH$_2$)$_8$CH$_3$;
= compound according to Formula (I), wherein R is —(CH$_2$)$_6$CH$_3$.

TABLE 2

Example concentrates of the third aspect

| | Example | | | | | | | | | | | | | | |
|---|---|---|---|---|---|---|---|---|---|---|---|---|---|---|---|
| | 10 | 11 | 12 | 13 | 14 | 15 | 16 | 17 | 18 | 19 | 20 | 21 | 22 | 23 | 23a |
| *N-Decanoyl-N-Methyl-Glucamide | 45 | 15 | 30 | 30 | 25 | 25 | 20 | — | 65 | 30 | 20 | 30 | 20 | 40 | 30 |
| #N-Octanoyl-N-Methyl-Glucamide | 45 | 15 | 30 | 30 | 25 | 25 | 20 | 65 | — | 30 | 40 | 65 | 40 | 20 | 30 |
| Octopirox | 10 | — | — | — | — | — | — | — | — | — | — | — | — | 5 | — |
| Phenoxyethanol | — | 70 | — | — | — | — | — | — | — | — | — | — | — | — | — |
| Benzyl alcohol | — | — | 40 | — | — | — | — | — | — | 25 | — | — | — | — | — |
| Phenetyl Alcohol | — | — | — | 40 | — | — | — | — | — | — | — | — | — | 5 | — |
| Benzoic Acid | — | — | — | — | 20 | — | — | — | 15 | — | — | — | — | — | — |
| Sodium Benzoate | — | — | — | — | — | — | — | — | — | — | 20 | — | — | — | — |
| Sorbic Acid | — | — | — | — | — | 20 | — | — | 15 | — | — | — | — | — | — |
| Potassium Sorbate | — | — | — | — | — | — | 25 | — | — | — | — | — | — | — | — |
| Dehydroacetic Acid | — | — | — | — | — | — | — | — | — | 14 | — | — | — | — | — |
| Tocopherol | — | — | — | — | 1 | — | 1 | — | 1 | — | 0.5 | — | 0.5 | — | |
| p-Anisic Acid | — | — | — | — | — | — | — | — | — | — | — | 20 | 10 | — | |
| Benzisothiazolone (BIT) | | | | | | | | | | | | | | | 2 |

TABLE 2-continued

Example concentrates of the third aspect

| | Example | | | | | | | | | | | | | | |
|---|---|---|---|---|---|---|---|---|---|---|---|---|---|---|---|
| | 10 | 11 | 12 | 13 | 14 | 15 | 16 | 17 | 18 | 19 | 20 | 21 | 22 | 23 | 23a |
| Perfume | — | — | — | — | — | — | 5 | — | — | — | — | 4.5 | — | 5 | — |
| Propanediol | — | — | — | — | 15 | 14 | 20 | — | 5 | — | 10 | — | 15 | — | — |
| Glycerine | — | — | — | — | — | 15 | 30 | — | — | — | — | — | — | 14.5 | — |
| Water | — | — | — | — | 15 | — | 5 | 9 | — | — | 10 | — | 5 | — | 38 |
| Total (%) | 100 | 100 | 100 | 100 | 100 | 100 | 100 | 100 | 100 | 100 | 100 | 100 | 100 | 100 | 100 |

KEY for Table 2:
*= compound according to Formula (I), wherein R is —$(CH_2)_8CH_3$;
= compound according to Formula (I), wherein R is —$(CH_2)_6CH_3$.

TABLE 3

Example formulations of the sixth aspect

| | Example | | | | |
|---|---|---|---|---|---|
| | 24 | 25 | 26 | 27 | 28 |
| Formulation | Liquid soap | Body wash | Wet wipe lotion | Shampoo | Shampoo |
| Concentrate of example 10 [1] | — | — | — | — | 2 |
| Concentrate of example 13 [1] | — | — | — | 1.5 | — |
| Concentrate of example 14 [1] | — | 2 | — | — | — |
| Composition 6 [2] | 1.5 | — | 1.0 | — | — |
| SLES | 10 | — | — | — | 9 |
| Cocamido-propylbetaine | 2 | 4.5 | — | — | 2 |
| Cocamide MEA | — | — | — | — | 1 |
| Sodium Cocoyl Glutamate | — | 2 | 1 | 2 | — |
| Sodium Cocoyl Glycinate | — | 2 | 1 | 2 | — |
| Sodium Cocoyl Isethionate | — | 2 | — | — | — |
| Cocoyl Methyl Glucamide | — | 3 | 2 | — | — |
| EGDS | — | 0.5 | — | — | 0.7 |
| PEG-7 Glyceryl Cocoate | — | — | 1 | — | — |
| Cocoyl glucoside | — | — | — | 5 | — |
| Lauryl Glucoside | — | — | — | 5 | — |
| Acrylates Copolymer | — | — | — | 2 | — |
| Glycerine | — | — | — | 1 | 2 |
| Panthenol | — | — | — | 0.2 | 0.2 |
| Dimethicone | — | — | — | — | — |
| Polyquaternium 7 (PQ-7) | — | — | — | — | 0.6 |
| Guar Hydroxypropyltrimonium Chloride | — | — | — | — | 0.3 |
| Hydrolyzed Protein | — | — | — | — | 0.1 |
| Perfume | 0.2 | 0.2 | 0.1 | — | 0.8 |
| NaCl | 1.5 | 1.0 | 0.5 | 0.3 | 1.5 |
| Water | QSP | QSP | QSP | QSP | QSP |
| Total | 100% | 100% | 100% | 100% | 100% |
| pH | 5.0 | 4.5 | 7 | 6.5 | ND |
| Viscosity (mPa · s) | 4000 | 3000 | 100 | 5500 | ND |

KEY:
[1] = see Table 2 above;
[2] = see Table 1 above;
ND = not determined.

| | Example | | | | |
|---|---|---|---|---|---|
| | 29 | 30 | 31 | 32 | 33 |
| Formulation | § | § | § | § | § |
| Concentrate of example 11 [1] | — | — | — | — | 2 |
| Concentrate of example 14 [1] | — | — | — | 1.5 | — |

TABLE 3-continued

| Example formulations of the sixth aspect | | | | | |
|---|---|---|---|---|---|
| Concentrate of example 15 [1] | — | 2 | — | — | — |
| Concentrate of example 23a [1] | 2 | — | 1.0 | — | — |
| Sodium lauryl ether sulfate (SLES) | 18 | 18 | 19 | 8 | — |
| Cocamidopropylbetaine | 8 | — | — | 4 | — |
| Sodium Alkane sulfonate | — | — | — | 24 | — |
| Lauryldimethylamine oxide | — | — | 6 | — | 5 |
| Ethanol | 7 | 4 | — | — | — |
| Coco-Glucamide | — | 8 | — | — | — |
| Perfume | 0.2 | 0.2 | 0.1 | 0.1 | 0.8 |
| Cumene sulfonate | — | — | 1.5 | — | — |
| Alpha-Olefine sulfonate (Na salt) | — | — | — | — | 15 |
| Water & auxiliaries | QSP | QSP | QSP | QSP | QSP |
| Total | 100% | 100% | 100% | 100% | 100% |
| pH value | 6.0 | 5.5 | 8.5 | 5.5 | 8.5 |

KEY:
[1] = see Table 2 above;
[2] = see Table 1 above;
§ = hand dishwashing formulation.

| | Example | | | |
|---|---|---|---|---|
| | 34 | 35 | 36 | 37 |
| Formulation | Body Lotion | Intensive hand and body lotion | Anti-ageing night cream | Baby cream |
| Concentrate of example 10 [1] | — | — | — | — |
| Concentrate of example 13 [1] | — | — | — | 1.5 |
| Concentrate of example 14 [1] | — | 2 | — | — |
| One of compositions 1 to 9 [2] | 1.5 | — | 1.0 | — |
| Ethyhexyl Stearate | 7 | — | — | — |
| Decyl Oleate | 5 | — | — | — |
| Plantasens ® Natural Emulsifier HE 20 (Clariant), which is Cetearyl Glucoside (and) Sorbitan Olivate | 3 | — | — | — |
| Dimethicone | 2 | — | — | — |
| Glycerin | 3 | 3 | 7 | — |
| Xanthan Gum | 0.2 | — | — | — |
| Aristoflex ® AVC from Clariant (Ammonium Acryloyldimethyltaurate/VP Copolymer) | 0.5 | 1 | — | — |
| Fragrance | 0.3 | — | 0.3 | 0.3 |
| Polyglyceryl-2-Sesquiisostearate | — | 0.5 | — | 2 |
| Trilaureth-4 Phosphate | — | 2 | — | — |
| Mineral Oil (Paraffinum Liquidum) | — | 5 | — | — |
| Plantasens ® Refined Organic Babassu Butter from Clariant (Orbignya Oleifera Seed Oil) | — | 2 | — | — |
| Squalane | — | 2 | 12 | — |
| Macadamia Ternifolia Seed Oil (and) Crambe Abyssinica Seed Oil (and) Orbignya Oleifera Seed Oil | — | 2 | — | — |
| Silcare ® Silicone SEA from Clariant (Trideceth-9 PG-Amodimethicone and Trideceth-12) | — | 0.5 | — | — |
| Cetearyl Alcohol | — | 2 | — | — |
| Isopropyl Palmitate | — | 4 | — | — |

TABLE 3-continued

| Example formulations of the sixth aspect | | | | |
|---|---|---|---|---|
| Dow Corning ® 345 (Cyclopentasiloxane and Cyclohexasiloxane) | — | — | 10 | — |
| Paraffin Oil, low viscosity | — | — | 4 | 10 |
| Petrolatum | — | — | 4 | 15 |
| Cetyl Alcohol | — | — | 3 | — |
| Cutina ® GMS (Glyceryl Stearate) | — | — | 2.5 | — |
| PEG-40 Stearate | — | — | 3 | — |
| Cera Alba Wax | — | — | 2 | — |
| Mangifera Indica (Mango) Seed Butter | — | — | 2 | — |
| Abyssinian Oil (and) Phytosterols (and) Olea Europea (Olive) Oil Unsaponifiables | — | — | 0.5 | — |
| Sorbitan Tristearate | — | — | 0.3 | — |
| Ubiquinone | — | — | 0.05 | — |
| Aristoflex ® Velvet from Clariant (Polyacrylate Crosspolymer-11) | — | — | 0.3 | — |
| Hostacerin ® SFO from Clariant (Sunflower Seed Oil Sorbitol Esters) | — | — | — | 3.5 |
| Paracera ® M (Cera Microcristallina) | — | — | — | 2 |
| Beeswax | — | — | — | 1 |
| Magnesium Stearate | — | — | — | 1 |
| Talc | — | — | — | 10 |
| Zinc oxide | — | — | — | 10 |
| Allantoin (Clariant) | — | — | — | 0.3 |
| Extrapon Hamamelis | — | — | — | 2 |
| D-Panthenol | — | — | — | 2 |
| Water | QSP | QSP | QSP | QSP |
| pH | pH 5 | pH 5.2-5.7 | ND | ND |
| Total | 100% | 100% | 100% | 100% |

KEY:
[1] = see Table 2 above;
[2] = see Table 1 above,
ND = not determined.

| | Example | | | | |
|---|---|---|---|---|---|
| | 38 | 39 | 41 | 42 | 43 |
| Formulation | $ | $ | $ | $ | $ |
| Concentrate of example 11 [1] | — | — | — | 2 | 2 |
| Concentrate of example 14 [1] | — | — | 2 | — | — |
| Concentrate of example 15 [1] | — | 2 | — | — | — |
| Any of compositions 1 to 23a [1] | 1 | — | — | — | — |
| Sodium lauryl ether sulfate (SLES) | 2 | 2 | 2 | — | — |
| Lauryldimethylamine oxide | 2 | — | — | — | 2 |
| Alkylbenzenesulfonate | — | — | — | 2 | 2 |
| Laureth-7 | — | — | 2 | 2 | — |

TABLE 3-continued

Example formulations of the sixth aspect

| | | | | | |
|---|---|---|---|---|---|
| Capric/Capryl-Glucamide | — | 2 | — | — | — |
| Perfume | 0.2 | 0.2 | 0.1 | 0.1 | 0.8 |
| Water & auxiliaries | QSP | QSP | QSP | QSP | QSP |
| Total | 100% | 100% | 100% | 100% | 100% |
| pH value | 80 | 5.0 | 5.5 | 7.0 | 8.5 |

KEY:
[1] = see Table 2 above;
[2] = see Table 1 above;
$ = hard surface cleaner

| | Example | | | | |
|---|---|---|---|---|---|
| | 38 | 39 | 41 | 42 | 43 |
| Formulation | & | & | & | & | & |
| Concentrate of example 11 [1] | — | 2 | — | 2 | 2 |
| One of compositions 1 to 23a [1] | 1 | — | 1 | — | — |
| Sodium lauryl ether sulfate (SLES) | 10 | 15 | 5 | 15 | 2 |
| Alkylbenzenesulfonate | 10 | 5 | 15 | 0 | 15 |
| Laureth-7 | 10 | 10 | 10 | 10 | 8 |
| C12/14 fatty acid soap | 3 | 3 | 3 | 5 | 5 |
| Perfume | 0.2 | 0.2 | 0.1 | 0.1 | 0.8 |
| Water & auxiliaries | QSP | QSP | QSP | QSP | QSP |
| Total | 100% | 100% | 100% | 100% | 100% |

KEY:
[1] = see Table 2 above;
[2] = see Table 1 above;
& = liquid laundry detergent formulation

| | Example | | | | | |
|---|---|---|---|---|---|---|
| | 44 | 45 | 46 | 47 | 48 | 49 |
| Formulation | Soap formulation | Soap bar | Body wash | Shampoo | Wash cream | Body wash |
| Concentrate of example 10 [1] | — | — | — | — | 1 | — |
| Concentrate of example 13 [1] | — | — | — | 1.5 | — | 0.8 |
| Concentrate of example 14 [1] | — | 2 | — | — | — | — |
| Composition 6 [2] | 1.5 | — | 1.0 | — | — | — |
| Sodium Lauryl Sulfate | — | — | 10 | — | — | — |
| Ammonium Lauryl Sulfate | — | — | — | 12 | — | — |
| Sodium lauryl ether sulfate (SLES) | 15 | — | 2 | — | — | — |
| Cocamido-propylbetaine | 7 | — | 2 | 3 | — | 2 |
| Cocamide MEA | — | — | 1 | — | — | 2 |
| Lauric Acid | 0.5 | 2 | — | — | — | 10 |
| Myristic Acid | 1.5 | 2 | — | — | — | 10 |
| Stearic Acid | 0.5 | 2 | — | — | 10 | — |
| Palmitic Acid | — | 2 | — | — | — | 10 |
| Potassium Tallowate | — | 2 | — | — | — | — |
| Sodium Palm Kernelate | — | 20 | — | — | — | — |
| Sodium Cocoate | — | 60 | — | — | — | — |
| Lauryl Glucoside | — | — | — | 4 | — | — |
| Sodium Cocoyl Isethionate | — | — | — | — | 14 | — |
| Glycerine | — | 5 | — | — | — | 5 |
| Cetearyl Alcohol | 1.5 | — | — | — | 2 | — |
| Dimethicone | — | — | — | — | 0.1 | — |
| Polyquaternium 7 (PQ-7) | — | — | — | 0.2 | — | — |
| Guar Hydroxypropyltrimonium Chloride | — | — | 0.3 | — | — | — |

TABLE 3-continued

Example formulations of the sixth aspect

| | | | | | | |
|---|---|---|---|---|---|---|
| Hydrolyzed Protein | — | — | — | 0.1 | — | — |
| Perfume | 1 | 0.2 | 0.1 | — | 0.8 | 0.7 |
| NaCl | 1.5 | — | 0.5 | 0.3 | — | 2.5 |
| Water | QSP | QSP | QSP | QSP | QSP | QSP |
| Total | 100% | 100% | 100% | 100% | 100% | 100% |
| pH | 6.5 | 4.5 | 7 | 6.5 | 8.5 | 9.5 |
| Viscosity (mPa · s) | 3000 | 3000 | 1000 | 5500 | 10000 | 2500 |

KEY:
[1] = see Table 2 above;
[2] = see Table 1 above;

Example Methods of Use of the Formulations: Example 1 in Table 3 is a shampoo formulation. Shampoo formulations of the present invention are used in a conventional manner for cleaning and conditioning hair or skin. For example, an effective amount of the composition for cleansing and conditioning the hair or skin is applied to the hair or skin, which has preferably already been wetted with water, and then rinsed off. Such effective amounts generally range from about 1 gram to about 50 gram, preferably from about 1 gram to about 20 gram. Application to the hair typically includes working the composition through the hair such that most or all of the hair is contacted with the composition. For example, for cleansing and conditioning the hair or skin comprises the steps of: a) wetting the hair or skin with water, b) applying an effective amount of the shampoo composition to the hair or skin, and c) rinsing the applied areas of skin or hair with water. These steps can be repeated as many times as desired to achieve the desired cleansing and/or conditioning benefit.

EXPERIMENTAL 1

For testing the inhibition of bacteria, Composition 6 from Table 1 above was diluted in butylpolyglycol and added in different concentrations to liquid Caso-Agar at 50° C. and is buffered to pH 7 (+/−0.2). For testing the inhibition of yeast and mold, the Composition 6 was diluted in butylpolyglycol and added in different concentrations to liquid Sabouraud-4% Dextrose-Agar at 50° C. and is buffered to pH 5.6 (+/−0.2). Each of the solutions is poured into a petri-dish and inoculated with the same amount of bacteria, yeast or mold respectively. The minimum inhibitory concentration (MIC) is the lowest concentration of Composition 6 that inhibits the growth of the respective microorganism where the next lowest dilution fails to inhibit the growth of said microorganism.

The experiments were carried out in scientifically fair conditions so that a proper comparison can be made and conclusions drawn.

TABLE 4

Table of MIC data:

| Organisms; Bacteria (B), Yeast (Y) and Mold (M) | MIC of Sorbitan Caprylate [ppm] | MIC of Composition 6 [ppm] |
|---|---|---|
| Staphylococcus aureus (B) | 800 | 600 |
| Pseudomonas aeruginosa (B) | 10000 | 10000 |
| Escherichia coli (B) | 10000 | 10000 |
| Enterobacter aerogenes (B) | 10000 | 10000 |
| Klebsiella pneumoniae (B) | 800 | 800 |

TABLE 4-continued

Table of MIC data:

| Organisms; Bacteria (B), Yeast (Y) and Mold (M) | MIC of Sorbitan Caprylate [ppm] | MIC of Composition 6 [ppm] |
|---|---|---|
| Enterobacter gergovia (B) | 10000 | 10000 |
| Citrobacter freundii (B) | 10000 | 10000 |
| Cornyebacterium jeikeium (B) | 4000 | 4000 |
| Cornyebacterium xerosis (B) | 2000 | 2000 |
| Brevibacterium linens (B) | 4000 | 4000 |
| Staph. Epidermis (B) | 10000 | 8000 |
| Streptococcus mutans (B) | 2000 | 2000 |
| Candida albicans (Y) | 800 | 10000 |
| Aspergillus brasiliensis (M) | 800 | 600 |
| Penicillium minioluteum (M) | 400 | 400 |
| Aspergillus terreus (M) | 800 | 8000 |
| Fusarium solani (M) | 800 | 400 |
| Penicillium funicolosium (M) | 400 | 2000 |
| Saccharomyces cerevisiae (Y) | 600 | 2000 |
| Candida parapsilosis (Y) | 800 | 8000 |
| Malassezia furfur (Y) | 600 | 400 |
| Malassezia pachydermatis (Y) | 400 | 600 |
| Malassezia sympiodalis (Y) | 400 | 400 |

Conclusions:

The data shows Composition 6's excellent performance towards a broad range of microorganisms. The MIC values are very strong against Staph. aureus, Klebsiella pneumonia, and the cornyebacteria. The latter are found on the human body in areas where a lot of sweat is produced, hence, an odor reduction of Composition 6 is concluded. The Composition 6 is strong against fungi, especially the Malassezia species, which are found on the human scalp, and the source of dandruff. Therefore, an activity against dandruff on human scalp is concluded.

The structure of Compound X is chemically more stable than comparable market standards (sorbitan caprylate, glyceryl caprylate) versus high/low pH as the amide bond is more stable than an ester bond. This enables use in broader range of formulations across the application areas, without compromising on performance.

The increased water solubility of Compound X is a feature, which is not found in the comparable market standards. This is highly appreciated by formulators, because it makes formulating the ingredient easier in all types of formulations containing water. The Compound X is less likely to precipitate/cream in the respective formulation, contributing not only to microbiological stability, but also ensures formulation stability.

The Compound X has a relatively high Hydrophilic Lipophilic Balance HLB value (Composition 6=HLB of 10.2) and this allows its use as a non-ionic emulsifier in emulsions and as a solubiliser for additives in all kinds of formulations.

EXPERIMENTAL 2

A similar experiment was carried out versus Experimental 1. The composition employed in this second experiment is almost identical in composition to Composition 6 from Table 1 above, differing only slightly in the exact levels of the components. Composition 6a is according to the first aspect of the present invention. Here, a comparison is made versus the efficacy of phenoxyethanol, alone and in combination with composition 6a.

TABLE 5

Table of MIC data:

| Organisms; Bacteria (B), Yeast (Y) and Mold (M) | MIC of Composition 6a [ppm] | MIC of Phenoxy- ethanol [ppm] | MIC of Composition 6a with Phenoxy- ethanol (1:1) [ppm] |
|---|---|---|---|
| Staphylococcus aureus (B) | <500 | 5000 | <500 |
| Pseudomonas aeruginosa (B) | >10000 | 4000 | 3000 |
| Escherichia coli (B) | >10000 | 4000 | 3000 |
| Enterobacter aerogenes (B) | >10000 | 4000 | 3000 |
| Klebsiella pneumoniae (B) | >10000 | 4000 | 1000 |
| Burkholderia cepacia (B) | 5000 | 1500 | 1000 |
| Enterobacter gergovia (B) | >10000 | 4000 | 3000 |
| Citrobacter freundii (B) | >10000 | 4000 | 3000 |
| Candida albicans (Y) | 4000 | 3000 | 1500 |
| Aspergillus brasiliensis (M) | 6000 | 2000 | 1500 |
| Penicillium minioluteum (M) | 1000 | 1000 | <500 |
| Aspergillus terreus (M) | 6000 | 3000 | 2000 |
| Fusarium solani (M) | 2000 | 2000 | 1000 |
| Penicillium funicolosium (M) | 1000 | 1000 | <500 |
| Saccharomyces cerevisiae (Y) | 1500 | 4000 | 1000 |
| Candida parapsilosis (Y) | >10000 | 3000 | 1500 |

Conclusions:

The data shows the MIC of Composition 6a, the MIC of Phenoxyethanol and the MIC of a 1:1 mixture of both ingredients towards the listed microorganisms. The MIC test consists of dilution experiments until the growth of the respective organism is inhibited, therefore the lower the MIC, the better. Without any synergistic effect, the mixtures should give a linear interpolation between the values of both neat products. In Table 5 it can be seen that the values versus all of the organisms are surprisingly lower than the bulk materials. This is a synergistic effect because the mixture is more active than the expected interpolation. This synergy is beneficial to save preservative and to protect formulations with reduced amount of preservative, as well as having access to preservatives that are too weak to use without a synergistic preservative booster.

What is claimed is:

1. A formulation comprising from 0.001 wt.-% to 20 wt.-% compound X, by total weight of the formulation, wherein compound X is according to Formula (I)

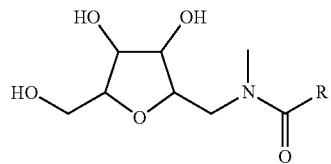

wherein R is a saturated or unsaturated hydrocarbon chain having seven or nine carbon atoms, or a mixture thereof.

2. The formulation according to claim 1, wherein the formulation comprises from 0.01 wt.-% to 10 wt.-% of compound X, by total weight of the formulation.

3. The formulation according to claim 1, wherein compound X is a mixture of compounds according to Formula (I) wherein R is —$(CH_2)_8CH_3$ or —$(CH_2)_6CH_3$.

4. The formulation according to claim 1, wherein the formulation is selected from the group consisting of cosmetic formulations and household cleansing formulations.

5. The formulation according to claim 1, wherein the formulation is a formulation selected from the group consisting of shampoo, body wash, facial cleanser, cleansing masks, bubble bath, bath oil, cleansing milk, micellar water, make-up remover, cleansing wipes, perfume, soaps, shaving soaps, shaving foams, cleansing foams, face mask, and body lotion.

6. The formulation according to claim 1, wherein the formulation is a hand dishwashing formulation, hard surface cleaner or liquid laundry detergent formulation.

7. The formulation according to claim 1, wherein the formulation further comprises a solvent, wherein the solvent comprises water and/or alcohol.

8. The formulation according to claim 1, wherein the formulation further comprises an oily substance.

9. The formulation according to claim 1, wherein the formulation further comprises a non-ionic coemulsifier.

10. The formulation according to claim 1, wherein the formulation further comprises a cationic polymer.

11. The formulation according to claim 1, wherein the formulation further comprises a conditioning agent.

12. The formulation according to claim 1, wherein the formulation further comprises a surfactant system.

13. The formulation according to claim 1, wherein the formulation further comprises a viscosity-modifying substance.

14. The formulation according to claim 1, wherein the formulation further comprises a thickening polymer.

15. The formulation according to claim 1, wherein the formulation further comprises a thickening polymer, wherein the thickening polymer is selected from the group consisting of homo- or copolymers of acrylamidomethyl-propanesulfonic acid and salts thereof.

16. The formulation according to claim 1, wherein the formulation has a pH value of from 2.0 to 12.0.

17. The formulation according to claim 1, wherein the formulation has a viscosity of from 0 cPs to 20,000 cPs.

18. The formulation according to claim 1, wherein the formulation further comprises a surfactant system selected from the group consisting of anionic surfactants, cationic surfactants, non-ionic surfactants, zwitterionic surfactants amphoteric surfactants and mixtures thereof.

19. The formulation according to claim 1, wherein the formulation further comprises a conditioning agent which is selected from the group consisting of a silicone, an organic conditioning oil, a cationic conditioning surfactant, a high melting point fatty compound, and combinations thereof.

* * * * *